(12) United States Patent
Takeuchi et al.

(10) Patent No.: US 8,030,645 B2
(45) Date of Patent: Oct. 4, 2011

(54) ELECTRONIC DEVICE, PROCESS FOR PRODUCING THE SAME AND ELECTRONIC EQUIPMENT MAKING USE THEREOF

(75) Inventors: Takayuki Takeuchi, Osaka (JP); Kenji Harada, Osaka (JP); Tomohiro Okuzawa, Osaka (JP); Nobuaki Kambe, Hyogo (JP); Jun Terao, Osaka (JP)

(73) Assignee: Panasonic Corporation, Osaka (JP)

( * ) Notice: Subject to any disclaimer, the term of this patent is extended or adjusted under 35 U.S.C. 154(b) by 527 days.

(21) Appl. No.: 11/577,951

(22) PCT Filed: Oct. 24, 2005

(86) PCT No.: PCT/JP2005/019525
§ 371 (c)(1),
(2), (4) Date: Mar. 17, 2009

(87) PCT Pub. No.: WO2006/046521
PCT Pub. Date: May 4, 2006

(65) Prior Publication Data
US 2009/0224231 A1 Sep. 10, 2009

(30) Foreign Application Priority Data
Oct. 25, 2004 (JP) .................................. 2004-310074

(51) Int. Cl.
*H01L 51/00* (2006.01)

(52) U.S. Cl. ...................... 257/40; 257/E51.041; 438/99
(58) Field of Classification Search .................... 438/99; 257/40, E51.041
See application file for complete search history.

(56) References Cited

U.S. PATENT DOCUMENTS

| | | | | |
|---|---|---|---|---|
| 5,079,595 A * | 1/1992 | Suzuki et al. | .................... | 257/40 |
| 5,500,537 A * | 3/1996 | Tsumura et al. | ................. | 257/40 |
| 6,326,640 B1 * | 12/2001 | Shi et al. | .......................... | 257/40 |
| 6,456,003 B1 | 9/2002 | Mori et al. | | |
| 2006/0145141 A1* | 7/2006 | Miura et al. | .................... | 257/40 |
| 2006/0208251 A1* | 9/2006 | Yoshizawa | ...................... | 257/40 |

(Continued)

FOREIGN PATENT DOCUMENTS

| | | |
|---|---|---|
| JP | 10-125924 | 5/1998 |
| JP | 2003-309307 | 10/2003 |

OTHER PUBLICATIONS

"High-Performance Bottom Electrode Organic Thin-Film Transistors", Kymissis et al., IEEE Transactions on Electron Devices, vol, 48, No. 6, Jun. 2001 pp. 1060 to 1064.

(Continued)

*Primary Examiner* — Angel Roman
(74) *Attorney, Agent, or Firm* — Hamre, Schumann, Mueller & Larson, P.C.

(57) ABSTRACT

An electronic device of the present invention includes at least one electrode (Au electrode 65) and an organic molecule layer (semiconductor layer 14) formed adjacent to the electrode, and in which charge transfers between the layer and the electrode. The organic molecule layer includes a plurality of first organic molecules containing a conjugated π electron that composes a π conjugate plane (64). A plurality of second organic molecules is bonded chemically to a surface of the electrode at an interface between the electrode and the organic molecule layer. The second organic molecule contains a conjugated π electron that composes a π conjugate plane (67*a*). The second organic molecule is a molecule having a structure in which the π conjugate plane (67*a*) and the surface of the electrode form an angle within a predetermined range when the second organic molecule is bonded chemically to the surface of the electrode.

38 Claims, 29 Drawing Sheets

U.S. PATENT DOCUMENTS

2009/0278116 A1* 11/2009 Yamate .......................... 257/40

OTHER PUBLICATIONS

"Technology for Improving Operation of Organic Transistors", Technical Information Institute Co., Ltd., 2003, pp. 87-102, Japan.

Application and Development of Organic Semiconductors, Yuji Yoshida, CMC Publishing Co., Ltd., 2003, pp. 195-208, Japan.

English translation of International Preliminary Report on Patentability with English translation of Written Opinion of the International Searching Authority, dated May 1, 2007.

* cited by examiner

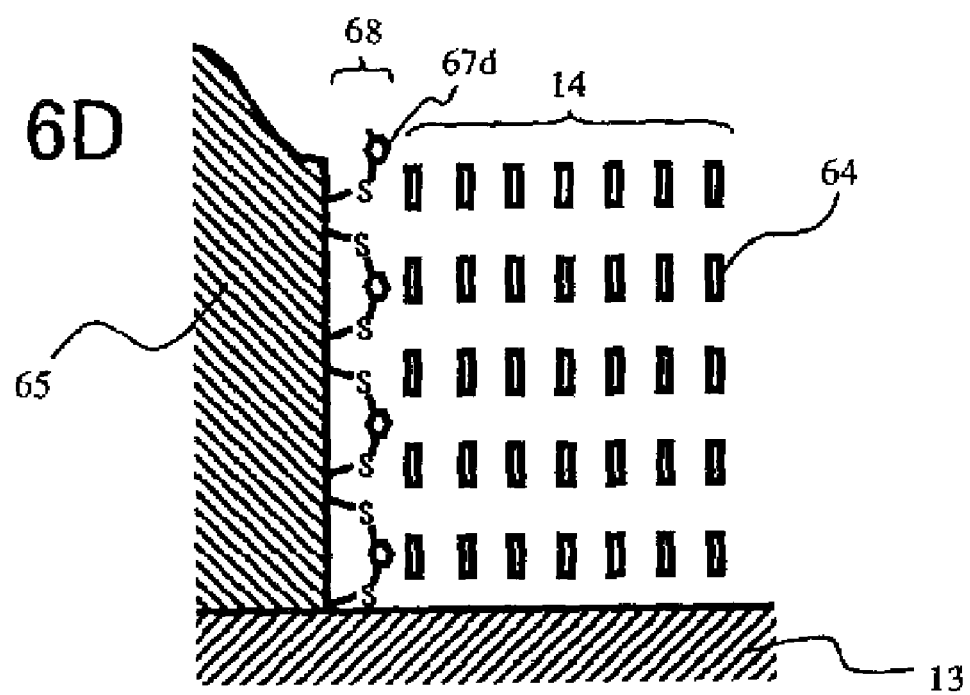

n=4~6

Fig. 14
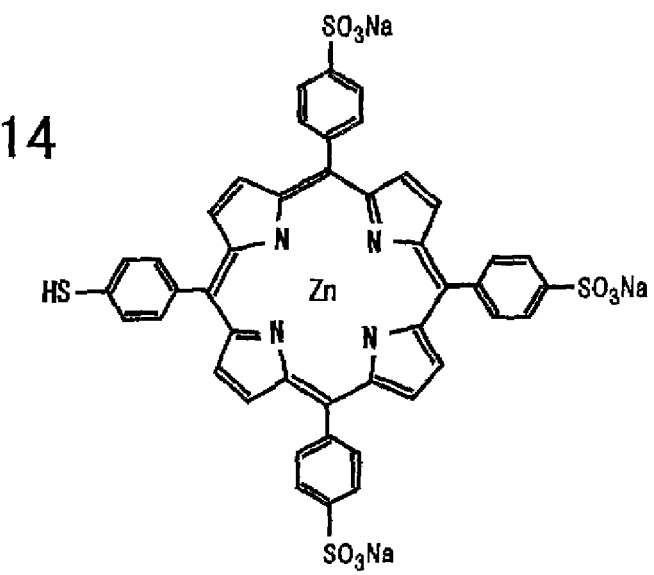
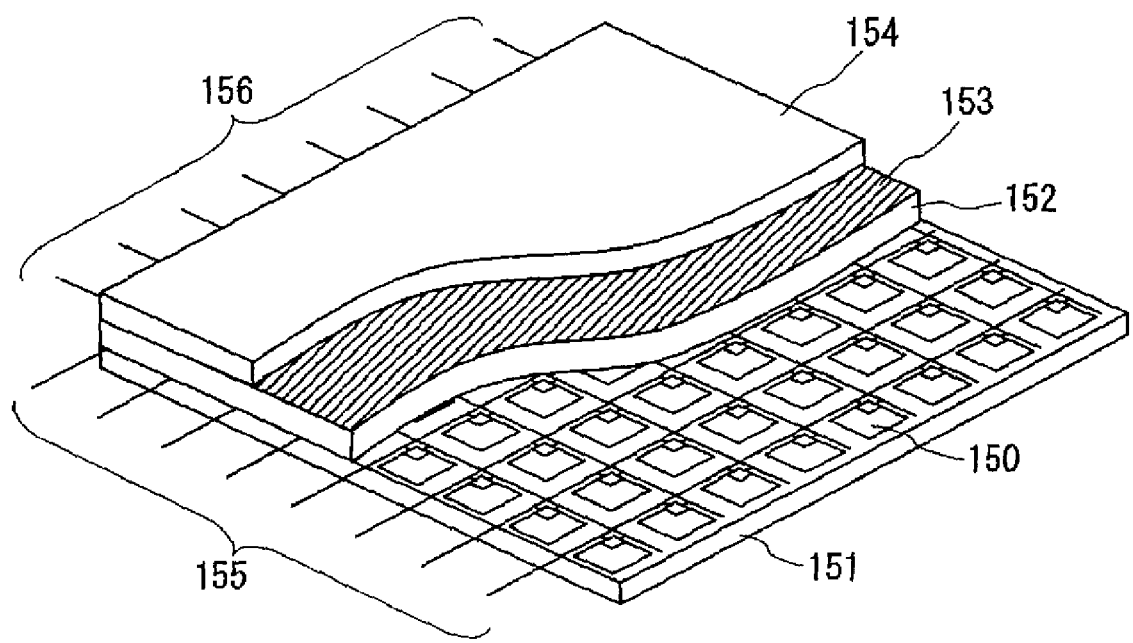
Fig. 15

ELECTRONIC DEVICE, PROCESS FOR PRODUCING THE SAME AND ELECTRONIC EQUIPMENT MAKING USE THEREOF

TECHNICAL FIELD

The present invention relates to an electronic device including an organic molecule layer, to a method of manufacturing the same and to an apparatus using the same.

BACKGROUND ART

Conventional electronic devices employing inorganic materials use physical properties of bulk materials, typically as crystalline silicon. When the scale of miniaturization reaches the utmost limit, it becomes impossible to obtain the bulk properties and difficult to obtain a desired function. On the other hand, organic materials can assign a function to one molecule and expand them into the device element size, and thereby they can exhibit the desired function.

Organic materials include various compounds having a base of a carbon skeleton. Among them, it was verified that organic molecules with conductivity exhibit diverse electric properties derived from their molecular structures, and proposals have been made for application on various organic electronic devices, such as thin film transistors, sensors, organic LEDs, capacitors, batteries, bio-functional devices, and lasers.

Thin film transistors (hereinafter also referred to as "TFTs") currently are expected to be useful drive elements for devices, such as active matrix liquid crystal displays. TFTs normally are formed of inorganic semiconductor materials, such as amorphous silicon and low-temperature polysilicon. Forming a semiconductor layer of a TFT by organic molecules enables reducing manufacturing costs and enlarging panel areas.

However, the organic semiconductors already been reported to have problems, such as having lower carrier mobility than those of inorganic semiconductors and causing high driving voltage when applied to device elements. For this reason, research has been carried out to improve the carrier mobility of organic semiconductors and to lower the driving voltage of device elements that employ organic semiconductors.

In most organic electronic devices that employ conductive organic molecules, sufficient device characteristics expected from the properties of conductive organic molecules can not be obtained. One possible factor is considered to be insufficient connectivity between electrodes and conductive organic molecules. As one of the methods to improve their electric connectivity, a method for easy charge transfer from an electrode to an organic semiconductor by disposing an organic layer (an electron transport layer or a positive hole transport layer) between the electrode and the organic semiconductor layer and for lowering the driving voltage of an organic TFT has been disclosed (JP10 (1998)-125924 A). A method of coating an electrode by any of a metal film, a conductive polymer film or a monomolecular film chemically bonded to the electrode for the purpose of reducing connection resistance between a conductive organic thin film and the electrode is disclosed (JP2003-309307).

The method described in JP10 (1998)-125924 A, however, requires a step, such as patterning, to form the organic layer at a predetermined position because the organic layer (the electron transport layer or the positive hole transport layer) is disposed as an intermediate layer independent from the electrode and the semiconductor layer. In addition, conventional techniques did not achieve sufficient improvement in electric connectivity between an electrode and an organic molecule layer, and thus a wide range of variations was found in the obtained characteristics in some cases.

DISCLOSURE OF INVENTION

With such a situation in mind, one of the objects of the present invention is to provide an electronic device having low connection resistance between an organic molecule layer and an electrode and having small variations in resistance, to provide a method of manufacturing the same and to provide various types of electronic apparatuses using the same.

In order to achieve the above-mentioned objects, the electronic device of the present invention is an electronic device that includes at least one electrode and an organic molecule layer formed adjacent to the electrode in which charge transfers between the layer and the electrode. The organic molecule layer includes a plurality of first organic molecules containing a conjugated $\pi$ electron that composes a $\pi$ conjugate plane (A). A plurality of second organic molecules is bonded chemically to a surface of the electrode at an interface between the electrode and the organic molecule layer. The second organic molecule contains a conjugated $\pi$ electron that composes a $\pi$ conjugate plane (B). The second organic molecule is a molecule having a structure in which the $\pi$ conjugate plane (B) and the surface of the electrode form an angle within a predetermined range when the second organic molecule is bonded chemically to the surface of the electrode.

Here, the angle within a predetermined range means a range of ±30° (preferably ±15°, more preferably ±7.5°) from a specific angle.

The first and the second organic molecules include a conjugated $\pi$ bond extended in two dimensions. The "$\pi$ conjugate plane" means a hypothetical plane including a conjugated bond formed by a conjugated $\pi$ electron and extended in two dimensions. From another perspective, the "$\pi$ conjugate plane" means a hypothetical plane including a plurality of atoms composing a conjugated $\pi$ bond. In some cases, the plurality of atoms composing a conjugated $\pi$ bond may exist not within one plane but in the neighboring area of a plane. In such a case, the "$\pi$ conjugate plane" may be defined as a hypothetical plane obtained by compressing, in the direction of thickness, a hypothetical rectangular parallelepiped including the plurality of those atoms.

The method of manufacturing an electronic device of the present invention is a method of manufacturing an electronic device provided with an organic molecule layer including a plurality of first organic molecules. The method includes (i) forming an electrode that has a plurality of second organic molecules chemically bonded to a surface thereof and the organic molecule layer that is adjacent to the electrode having the second organic molecules in between. The first organic molecule contains a conjugated $\pi$ electron that composes a $\pi$ conjugate plane (A). The second organic molecule contains a conjugated $\pi$ electron that composes a $\pi$ conjugate plane (B). The second organic molecule is a molecule having a structure in which the $\pi$ conjugate plane (B) and the surface of the electrode form an angle within a predetermined range when the second organic molecule is bonded chemically to the surface of the electrode.

In the electronic device of the present invention, since the second organic molecules are disposed on the electrode surface in order to align the direction of the $\pi$ conjugate planes formed by the conjugated $\pi$ electrons, a stable charge transfer utilizing overlaps between the second organic molecule and the $\pi$ conjugate planes of the adjacent first organic molecule is achieved. As a result, the connection resistance between the electrode and the conductive organic molecule layer, and its variations, can be reduced. In addition, since the second organic molecule is bonded chemically to the electrode, interfacial peeling and the like can be restricted. Thus, according to the present invention, an electronic device (an organic electronic device) having low connection resistance between an electrode and a conductive organic molecule layer and having the connection resistance with small variations can be obtained. In the case of the electronic device of the present invention being a TFT, a TFT having a low driving voltage can be obtained. Since the electronic device of the present invention does not require patterning the organic molecule layer formed on the electrode, it is manufactured easily. Since the electronic apparatus of the present invention uses the electronic device of the present invention (TFT), it has characteristics such as flexibility.

BRIEF DESCRIPTION OF DRAWINGS

FIG. 6D is a cross-sectional view that schematically shows still another example of the orientations of the first and the second organic molecules in the neighboring area of the channel region and the electrode.

FIG. 14 is a chemical formula that shows another example of the organic molecule modifying the source and the drain electrodes.

FIG. 15 is a partially exploded perspective view that schematically shows an example of the active matrix display of the present invention.

BEST MODE FOR CARRYING OUT THE INVENTION

Figure 1A:
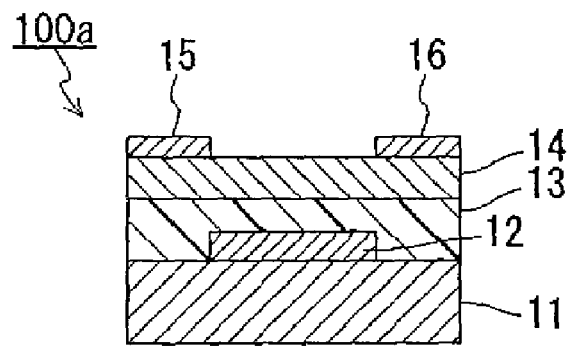
FIGS. 1A to 1D are cross-sectional views that schematically show an example of the TFT of the present invention.

Hereinafter, embodiments of the present invention are described.

[Electronic Device]

The electronic device of the present invention includes at least one electrode and an organic molecule layer formed adjacent to the electrode, and in which charge transfers between the layer and the electrode. The organic molecule layer includes a plurality of first organic molecules containing a conjugated π electron that composes a π conjugate plane (A). A plurality of second organic molecules is bonded chemically to a surface of the electrode at an interface between the electrode and the organic molecule layer. The second organic molecule contains a conjugated π electron that composes a π conjugate plane (B). The second organic molecule is a molecule having a structure in which the π conjugate plane (B) and the surface of the electrode form an angle within a predetermined range when the second organic molecules are bonded chemically to the surface of the electrode.

The organic molecule layer is composed of the first organic molecules, and the layer may include a substance other than the first organic molecule as long as the effects of the present invention may be obtained. The first organic molecule may contain a plurality of types of organic molecule, but it typically contains a single type of organic molecule. The organic molecule layer including the first organic molecule functions as a conductive or semiconductive layer. The first organic molecule is not particularly limited as long as it can form such a layer.

The first organic molecule is a molecule composing an organic conductive layer and an organic semiconductive layer. An example of the first organic molecule is described in the Embodiment 1.

The second organic molecule is chemically bonded to the surface of the electrode. Here, the chemical bond includes bonds such as a covalent bond, a coordinate bond and an ionic bond. The second organic molecule has the structure in which its surface and the π conjugate plane (B) form an angle within a predetermined range when they are chemically bonded to the surface of the electrode. An example of such a structure is a structure in which a mercapto group is bonded to the π conjugate plane (B). The angle formed by the π conjugate plane (B) and the electrode surface varies depending on the number and position of the mercapto group that bonds the π conjugate plane (B) and the electrode surface.

The second organic molecule may contain another conjugated π electron in addition to the conjugated π electron that forms the π conjugate plane (B). It is preferable that the second organic molecule contains a group easily bonded to the atom composing the electrode surface. An example of the second organic molecule is described in the Embodiment 1. The second organic molecule may contain a plurality of types of organic molecule, but it typically contains a single type of organic molecule.

The material for the electrode to which the second organic molecule is chemically bonded is not particularly limited, but at least the surface of the electrode includes an atom to which the second organic molecule can be chemically bonded. The electrode can be formed of a metal or a conductive metal oxide, for example.

In the electronic device of the present invention, an angle formed by the π conjugate plane (A) of the first organic molecule and the π conjugate plane (B) of the second organic molecule is preferably within a range from 0° to 30° (more preferably a range from 0° to 15°). Thus, when the π conjugate plane of the second organic molecule and the π conjugate plane of the first organic molecule are close to parallel, since these two planes easily face each other, it is possible to lower further the connection resistance between the electrode and the organic molecule layer.

In the electronic device of the present invention, the angle formed by the π conjugate plane (B) of the second organic molecule and the surface of the electrode may be within a range from 0° to 15° (preferably a range from 0° to 5°) or a range from 75° to 90° (preferably a range from 85° to 90°). When the π conjugate plane (B) of the second organic molecule and the surface of the electrode are almost parallel or almost perpendicular, since the second organic molecule can be designed with more flexibility and the angles formed by the π conjugate planes (B) of the second organic molecules and the surfaces of the electrodes can be aligned easily, an electronic device with stable characteristics can be obtained.

The first organic molecule can be oriented by a known method in a predetermined direction relative to the surface on which it is disposed. It is possible, for example, to orient the first organic molecules in order that the π conjugate planes (A) of the first organic molecules become almost perpendicular or almost parallel relative to the disposed surface. For this reason, defining the predetermined angle as the range above makes it easier to have the angle formed by the π conjugate plane (A) of the first organic molecule and the π conjugate plane (B) of the second organic molecule within a range from 0° to 30°.

The method for controlling the orientation of the first organic molecule is known, and the methods described in "Technology for Improving Operation of Organic Transistors" (Technical Information Institute Co., Ltd., 2003, 87-102, Japan) and "Application and Development of Organic Semiconductors" (CMC Publishing Co., Ltd., 2003, 195-208, Japan) may be applicable, for example.

In the electronic device of the present invention, the conjugated π electron composing the π conjugate plane (B) may exist in a condensed ring structure or a macrocyclic structure. The condensed ring structure may employ, for example, an aromatic polycyclic condensed ring, such as naphthalene, anthracene, perylene and pyrene, and the condensed ring may employ a heterocyclic compound, such as quinoline or carbazole. The macrocyclic structure is a large cyclic structure including a plurality of rings, and a cyclic structure of porphyrin may be an example.

In the electronic device of the present invention, the second organic molecule preferably forms a monomolecular layer. The monomolecular layer may include a substance other than the second organic molecule. When the second organic molecule forms the monomolecular layer, the effect of an electrode modifying layer formed by the second organic molecule on the physical properties of the organic molecule layer can be restrained.

In the electronic device of the present invention, the second organic molecules may be bonded to the electrode surface at predetermined intervals to each other. According to this configuration, since the effects of the second organic molecule can be obtained homogeneously on the electrode surface, the stability of the characteristics of the electronic device is improved.

In the electronic device of the present invention, the second organic molecules may be bonded to a plurality of atoms on the surface of the electrode. According to this configuration, since the electrode modifying film (a layer of the second organic molecules) is bonded more firmly to the electrode, an electronic device with highly stable characteristics can be obtained. In addition, by varying the lengths between the π conjugate plane (B) of the second organic molecule and a plurality of bondings, it becomes possible to align the π conjugate planes at an arbitrary angle. Still in addition, by chemically bonding at a plurality of points, it becomes possible to reduce the overlaps of the second organic molecules and to control the density of the second organic molecules on the electrode surface easily.

When three or more of substituents are bonded to the cyclic structure having the π conjugate plane (B), by bonding the second organic molecules to the electrode surface via the plurality of substituents, it becomes possible to form the π conjugate plane (B) and the electrode surface almost parallel to each other and to shorten the distance between the π conjugate plane (B) and the electrode surface.

In the electronic device of the present invention, the second organic molecules may be insulated by a cyclic molecule. Since molecular chains, connecting the π conjugate plane (B) and the electrode by the cyclic molecule, are insulated and thus the environmental resistance at the neighboring area is improved, the stability of the characteristics of the electronic device is improved. In addition, since the second molecules are limited in approaching each other due to the cyclic molecules, it becomes possible to control easily the density of the second organic molecules on the electrode surface. Still in addition, since the clathrate by the cyclic molecules enhances the linearity of the second organic molecules, it becomes easier to align the π conjugate planes perpendicular to the electrode surface.

In the electronic device of the present invention, the second organic molecules may be bonded to the atom of the electrode surface via a sulfur atom.

In the electronic device of the present invention, the second organic molecules may be porphyrin. In addition, in the electronic device of the present invention, the organic molecule layer may be an organic semiconductor layer or a conductive layer.

In the electronic device of the present invention, the organic molecule layers may be semiconductor layers, and the electronic device may include a plurality of electrodes making contact with the organic molecule layers and an electric field applying electrode to apply an electric field to the organic molecule layer. The electric field applying electrode is formed on at least one surface of the organic molecule layer via an insulating layer. That is, they are disposed in the order of the organic molecule layer/the insulating layer/the electric field applying electrode. According to this configuration, a current that flows through the plurality of electrodes making contact with the organic molecule layer can be controlled by the electric field applied to the organic molecule layer. For this reason, the stability of the characteristics of the electronic device using the field effects of the organic molecule layer (the semiconductor layer) can be improved.

The electronic device of the present invention further may include a gate electrode that applies an electric field to the organic molecule layer, the electrode may be at least one electrode selected from a source electrode and a drain electrode, the organic molecule layer may form a channel region, and the electronic device may function as a field-effect transistor. According to this configuration, since charge transfer between the organic molecule layer and the source and/or the drain electrodes becomes easier, an organic thin film transistor (an organic TFT) having a high carrier mobility and a low driving voltage can be obtained.

In the field-effect transistor of the present invention, although the second organic molecules preferably are bonded to both the source and the drain electrodes, the effects of the present invention may be obtained even when the second organic molecules are bonded to only one of the electrodes. In addition, although the effects of the present invention may be obtained when the second organic molecules are bonded to the part of the electrode surface making contact with the channel region, the second organic molecules also may be bonded to the entire electrode surface.

From another perspective, the electronic device of the present invention is an electronic device that includes at least one electrode and an organic molecule layer formed adjacent to the electrode, and in which charge transfers between the layer and the electrode. The organic molecule layer includes first organic molecules containing a conjugated π electron. Second organic molecules are bonded chemically to a surface of the electrode at an interface between the electrode and the organic molecule layer. The second organic molecule contains a conjugated π electron. The π conjugate plane formed by the conjugated π electron and the surface of the electrode are aligned to form a predetermined angle. Here, to be "aligned to form a predetermined angle" means that the molecular structures of the second organic molecule, the structures of the clathrate compound and the like are defined in order that the angle between the π conjugate plane of the second organic molecule and the electrode surface forms a predetermined angle. Therefore, this electronic device may partially include π conjugate planes forming irregularly varying angles due to the restrictions on manufacture (for example, a π conjugate plane forming a different angle due to an effect of impurities mixed in when modifying the electrode by the second organic molecule or due to an effect of impurities on the electrode surface or a structural defect). The "predetermined angle" may be a certain range of angles, and it may be, for example, angles in a range of about ±30° (preferably about ±15°) from a specific angle.

[Electronic Apparatus]

The electronic apparatus of the present invention includes a field-effect transistor, and the field-effect transistor is the field-effect transistor according to the present invention. The electronic apparatus of the present invention may include a field-effect transistor other than the field-effect transistor of the present invention. Hereinafter, the electronic apparatus of the present invention is described in detail by giving examples in the forms of an active matrix display, a wireless ID tag and a portable apparatus.

The active matrix display of the present invention includes a plurality of switching elements to drive a pixel, and these switching elements are the electronic devices (field-effect transistors) of the present invention. The pixels are driven by the switching elements. According to this configuration, a sheet-like or a paper-like display low in cost and having excellent characteristics can be achieved.

The wireless ID tag of the present invention includes a plurality of semiconductor elements, and at least a part of the plurality of semiconductor elements is the electronic device (field-effect transistor) of the present invention. The field-effect transistor of the present invention is, for example, used as a part of semiconductor elements configuring an integrated circuit of a wireless ID tag. According to such configuration, a wireless ID tag that can be applied on substances and materials with various shapes can be obtained. In addition, according to this configuration, a wireless ID tag that can be formed in an arbitrary shape can be achieved.

The portable apparatus of the present invention includes a plurality of semiconductor elements, and at least a part of the plurality of semiconductor elements is the electronic device (field-effect transistor) of the present invention. The field-effect transistor of the present invention is, for example, used as a part of semiconductor elements composing an integrated circuit of a portable apparatus. According to such configuration, it is possible to add advantages, such as low cost, flexibility, high impact resistance and ability to assume an arbitrary shape, to portable apparatuses such as portable televisions, communication terminals, PDAs and portable medical apparatuses.

[Method of Manufacturing an Electronic Device]

The method of manufacturing an electronic device of the present invention is a method of manufacturing an electronic device provided with an organic molecule layer including a plurality of first organic molecules. The method includes a step (i) forming an electrode that has a plurality of second organic molecules chemically bonded to a surface thereof and the organic molecule layer that is adjacent to the electrode having the second organic molecules in between. The first and the second organic molecules and the electrode employed for this manufacturing method are the same as those of the electronic device of the present invention. That is, the first organic molecule contains a conjugated $\pi$ electron that composes a $\pi$ conjugate plane (A). The second organic molecule contains a conjugated $\pi$ electron that composes a $\pi$ conjugate plane (B). The second organic molecule is a molecule having a structure in which the $\pi$ conjugate plane (B) and the surface of the electrode form an angle within a predetermined range when the second organic molecule is bonded chemically to the surface of the electrode. According to the manufacturing method of the present invention, the electronic device of the present invention can be manufactured.

Three examples of the step (i) are given below. The step (i) of a first manufacturing method includes an electrode modifying step in which the second organic molecules are chemically bonded to a surface of the electrode and a step of forming an organic molecule layer including first organic molecules on second organic molecules.

The step (i) of a second manufacturing method includes a step of forming an organic molecule layer including first organic molecules, a step of disposing second organic molecules on the organic molecule layer and an electrode modifying step in which the second organic molecules are chemically bonded to a surface of the electrode by forming the electrode on the second organic molecules.

The step (i) of a third manufacturing method includes a step of forming an electrode on a substrate, a step of modifying the electrode in which second organic molecules are chemically bonded to a surface of the electrode and a step of depositing the electrode on an organic molecule layer by attaching a surface side of the electrode modified by the second organic molecules to the organic molecule layer. By attaching the electrode to the organic molecule layer and then peeling off the substrate from the electrode, the electrode can be transferred to the organic molecule layer side.

In the first to third manufacturing methods described above, the second organic molecules are bonded to the surface of the electrode in order that the $\pi$ conjugate planes (B) of the second organic molecules and the surface of the electrode form a predetermined angle.

In the manufacturing method of the present invention, by selecting materials for the electrode and the second organic molecules bonded to it, the plurality of the second organic molecules are bonded to the electrode surface in order that each of their $\pi$ conjugate planes (B) form a predetermined angle relative to the surface of the electrode. Therefore, a stable charge transfer utilizing the overlaps between the $\pi$ conjugate planes of the first and the second organic molecules is achieved, and as a result, an electronic device with small variations in characteristics can be manufactured. In addition, according to this method, steps such as patterning are not required, which enables an easier formation of the monomolecular layer on the electrode surface. Accordingly, an electrode modifying film that is free from troubles such as an interfacial peeling and does not affect the original physical properties of the organic molecule layer composed of the first organic molecules can be obtained easily.

In the manufacturing method of the present invention, an angle formed by the $\pi$ conjugate planes (A) of the first organic molecules and the $\pi$ conjugate planes (B) of the second organic molecules is preferably within a range from 0° to 30°. According to this method, since the $\pi$ conjugate planes of the first organic molecules that compose the organic molecule layer and the $\pi$ conjugate planes of the second organic molecules easily face each other, an electronic device that has a smaller connection resistance between the electrode and the organic molecule layer can be manufactured.

In the manufacturing method of the present invention, an angle formed by the $\pi$ conjugate plane (B) of the second organic molecules and the surface of the electrode is preferably within a range from 0° to 15° or a range from 75° to 90°.

In the manufacturing method of the present invention, the conjugated $\pi$ electron composing the $\pi$ conjugate plane (B) may exist in a condensed ring structure or a macrocyclic structure.

In the method of the present invention, the second organic molecule may be self-assembled and may be bonded chemically to the surface of the electrode. According to this method, since the plurality of the second organic molecules can face each other easily, an electronic device having even smaller variations in characteristics can be manufactured.

In the manufacturing method of the present invention, the second organic molecule may contain a plurality of functional groups bonded to an atom existing of the electrode surface, and the second organic molecule may be bonded to a plurality of atoms of the electrode surface. According to this method, since the electrode modifying film (a layer of the second organic molecules) is bonded more firmly to the electrode, an electronic device with highly stable characteristics can be manufactured. In addition, by varying the lengths between the $\pi$ conjugate plane formed by the conjugated $\pi$ electron of the second organic molecule and a plurality of bondings, it becomes possible to align the $\pi$ conjugate planes at an arbitrary angle. Still in addition, by chemically bonding at a plurality of points, it becomes possible to reduce the overlaps of the second organic molecules and to control the density of the second organic molecules on the electrode surface easily.

The manufacturing method of the present invention may include, before the step (i), a step of insulating the second organic molecule by a cyclic molecule through mixing the second organic molecule and the cyclic molecule in a solvent, and the second organic molecule insulated by the cyclic molecule may chemically bond the electrode. According to this configuration, since the environmental resistance at the neighboring area of the second organic molecules insulated by the cyclic molecule is improved, the stability of the characteristics of the electronic device is improved. In addition, since the approach of the second organic molecules to each other is restricted by the cyclic molecules, it becomes possible to control the density of the second organic molecules on the electrode surface easily. Still in addition, since the clathrate by the cyclic molecules enhances the linearity of the second organic molecules, it becomes easier to align the $\pi$ conjugate planes perpendicular to the electrode surface.

In the manufacturing method of the present invention, the second organic molecule may be bonded to an atom on the surface of the electrode via a sulfur atom.

Hereinafter, Embodiments of the present invention are described. The present invention, however, is not limited to the following Embodiments. A part of the methods of manufacturing compounds mentioned in the Embodiments below are described later. In some of the figures referenced in the description below, hatching may be omitted.

Embodiment 1

In Embodiment 1, a case in which an oligothiophene derivative is employed as the first organic molecule composing the semiconductor layer of the TFT is described.

FIGS. 1A to 1D are cross-sectional views that schematically show a typical example of the TFT of the present invention. As shown in FIGS. 1A to 1D, the TFT of the present invention has various configurations. Any of these TFTs is provided with a substrate 11, a gate electrode 12, a gate insulating layer 13, a semiconductor layer (an organic molecule layer) 14, a source electrode 15, a drain electrode 16 and an electrode modifying layer (not shown). The gate electrode 12 faces the semiconductor layer 14 having the gate insulating layer 13 in between. An electric field applied to the semiconductor layer 14 by the gate electrode 12 controls turning on or off. The electrode modifying layer is composed of the second organic molecules, and the semiconductor layer 14 of the first organic molecules.

Figure 1B:
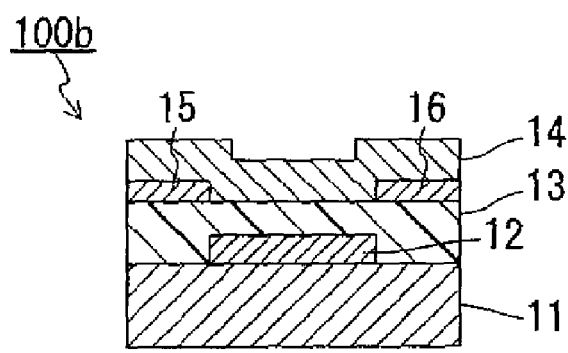
Figure 1C:
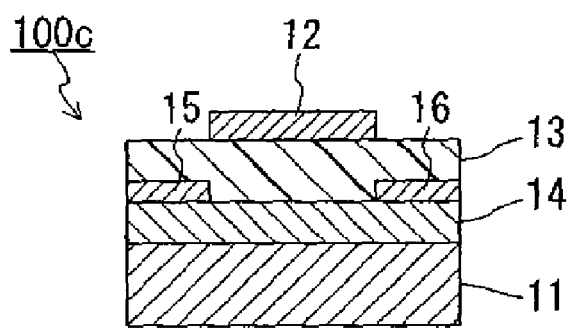
Figure 1D:
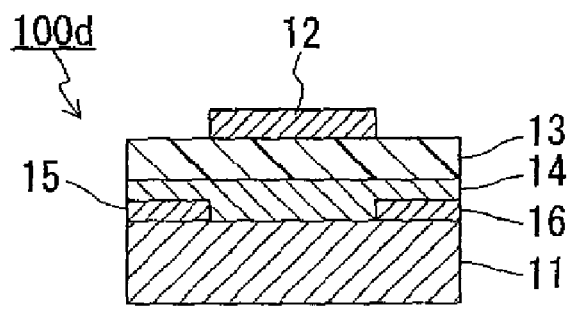

Generally, TFT 100a in FIG. 1A and TFT 100c in FIG. 1C are known as top contact TFTs. TFT 100b in FIG. 1B and TFT 100d in FIG. 1D are known as bottom contact TFTs. Since the TFTs 100b and 100d enable an easy formation of the electrode modifying layers, the present invention can be applied easily to them.

Figure 2A:
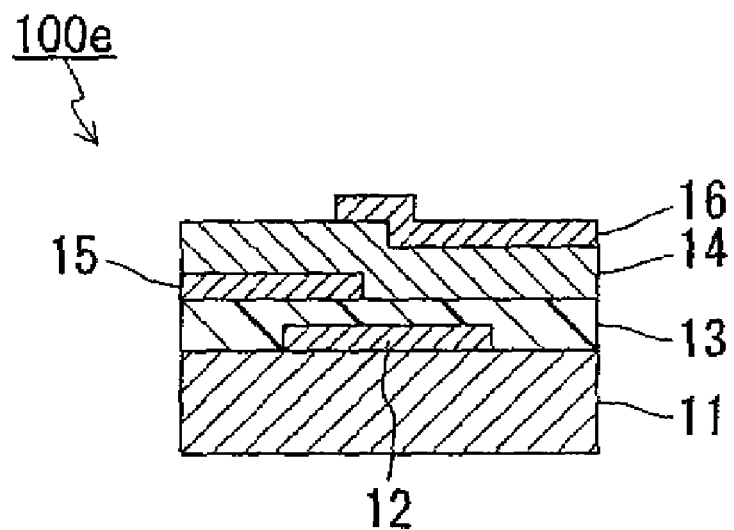
FIGS. 2A and 2B are cross-sectional views that schematically show another example of the TFT of the present invention.
Figure 2B:
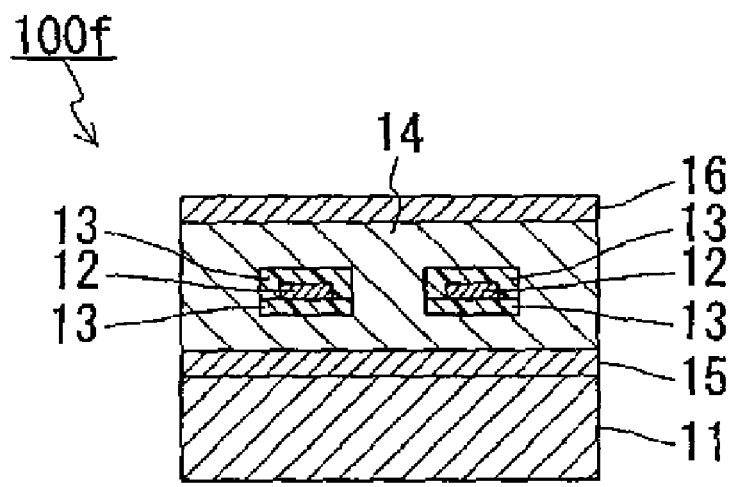

The TFT of the present invention may have a configuration as shown in FIGS. 2A and 2B. In TFTs 100e and 100f in FIGS. 2A and 2B, respectively, the source electrodes 15 and the drain electrodes 16 face each other and have the semiconductor layers 14 in between.

The TFTs shown in FIGS. 1 and 2 are examples, and the present invention is not limited to them. In addition, although the description below mainly discusses a case in which electrode modifying layer is formed at each of the interfaces between the semiconductor layer 14 and the source electrode 15 and between the semiconductor layer 14 and the drain electrode 16, the TFT of the present invention is not limited to this and it may have an electrode modifying layer formed only between the semiconductor layer 14 and either one of the electrodes.

As an example, the TFT 100b in FIG. 1B is described in the following. As shown in FIG. 1B, the gate electrode 12 is formed on a principal plane of the substrate 11, and the gate insulating layer 13 is formed to cover the gate electrode 12. The source electrode 15 and the drain electrode 16 are formed on the gate insulating layer 13 leaving spaces between them. Electrode modifying layers (not shown) are formed on the surfaces of the source electrode 15 and the drain electrode 16. Organic molecules composing the electrode modifying layers are bonded chemically to atoms of the electrode surfaces, and π conjugate planes of the organic molecules mostly are aligned in order that the planes and the surfaces of the electrodes form a predetermined angle. The semiconductor layer 14 containing π electron conjugate system molecules (the first organic molecules) as its main component is formed to cover the two electrodes and the gate insulating layer 13. In this way, the gate electrode 12, the gate insulating layer 13, the two electrodes and the semiconductor layer 14 are stacked on the substrate 11 in the TFT 100b.

In the TFT 100b, the electrode modifying layers are formed on the surface, adjacent to the semiconductor layer 14, of the entire surface of the source electrode 15 and the surface, adjacent to the semiconductor layer 14, of the entire surface of the drain electrode 16. These electrode modifying layers lower the connection resistance between the semiconductor layer 14 and the source and the drain electrode 15 and 16.

As an example, the TFT 100d shown in FIG. 1D is described in the following. In the TFT 100d, the source electrode 15 and the drain electrode 16 are formed on a principal plane of the substrate 11 leaving certain spaces between them. Electrode modifying layers (not shown) are formed on the surfaces of the source electrode 15 and the drain electrode 16. Organic molecules composing the electrode modifying layers are bonded chemically to atoms of the electrode surfaces, and π conjugate planes of the organic molecules are aligned in order that the planes and the surfaces of the electrodes form a predetermined angle. The semiconductor layer 14 is formed to cover the two electrodes and the substrate 11. The gate insulating layer 13 is formed on the semiconductor layer 14. The gate electrode 12 is formed on a place, which is on the gate insulating layer 13 and at least corresponds to the region between the source electrode 15 and the drain electrode 16. In this way, the TFT 100d has the two electrodes, the semiconductor layer 14, gate insulating layer 13 and the gate electrode 12 deposited on the substrate 11.

Three examples of the TFT of the present invention are specifically described below.

First Example

An example of manufacturing the TFT 100b shown in FIG. 1B is described as a First Example. In this Example, a polyethylene terephthalate (hereinafter, also referred to as "PET") film was employed as the substrate 11. The gate electrode 12 was formed by nickel (Ni), and the source and the drain electrodes 15 and 16 were formed by a material that contains gold (Au) as its main component. The organic molecules composing the electrode modifying layers are described later. The gate insulating layer 13 was formed by polyvinyl alcohol. The semiconductor layer 14 was formed by an oligothiophene derivative, which is one of π electron conjugate system molecules.

Figure 3A:
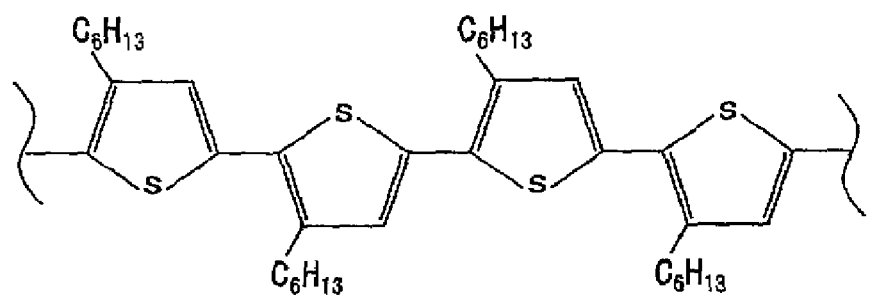
FIG. 3A is a drawing that shows the chemical formula of an oligothiophene derivative employed for the semiconductor layer.
Figure 3B:
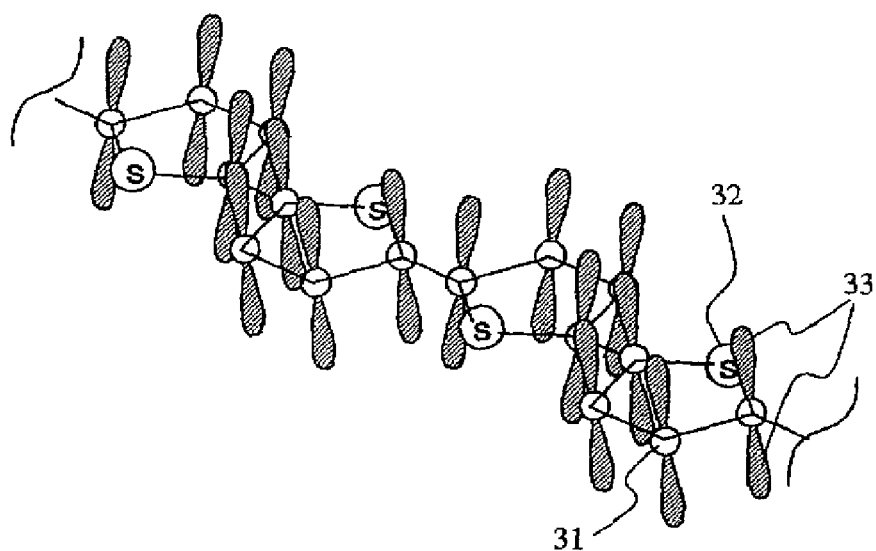
FIG. 3B is a drawing that shows the σ bond and the π electron cloud of the same and FIG. 3C is a perspective view that schematically shows the π conjugate plane of the same.
Figure 3C:
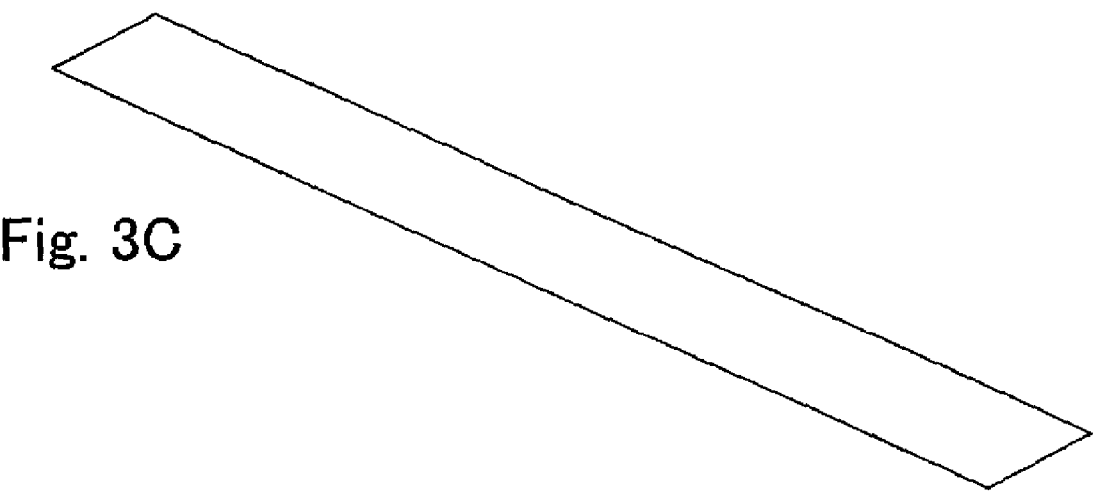

FIG. 3A shows the molecular structure of the oligothiophene derivative composing the semiconductor layer 14. FIG. 3B schematically shows the state of a bond and π electron cloud of the oligothiophene derivative. FIG. 3C is a perspective view that schematically shows the π conjugate plane of the oligothiophene derivative with the π electron cloud formed in the direction shown in FIG. 3B. It should be noted that the ends of the main chain of the oligothiophene derivative are omitted from the drawing in FIG. 3A. The ends of the main chain and the chemical structure of the side chains of the oligothiophene derivative are also omitted from the drawing in FIG. 3B.

As shown in FIG. 3A, five-membered rings including sulfur atoms (S) and having double bonds were bonded repeatedly by the σ bond and a π conjugate system was developed in the main chain of the oligothiophene derivative.

In the oligothiophene derivative, each five-membered ring is not present in the same plane, but the rings are bonded somewhat torsionally to each other by the σ bond. As a result, the π conjugate planes of each five-membered ring are not always aligned in parallel. The π conjugate plane formed by all of the five-membered rings, however, can approximate a plane, such as that schematically shown in FIG. 3C. The figures mentioned in the description below also may indicate a π conjugate plane by a plane similar to that shown in FIG. 3C.

In the First Example, an oligothiophene derivative in which a side chain was introduced to an oligothiophene molecule was employed. Specifically, regioregular type (hereinafter, also referred to as a "RR-") poly(3-hexyl thiophene) to which an alkyl group ($—C_6H_{13}$, in this Example) was bonded in a specific position of the five-membered rings including the sulfur atoms as shown in FIG. 3A was employed.

Figure 4:
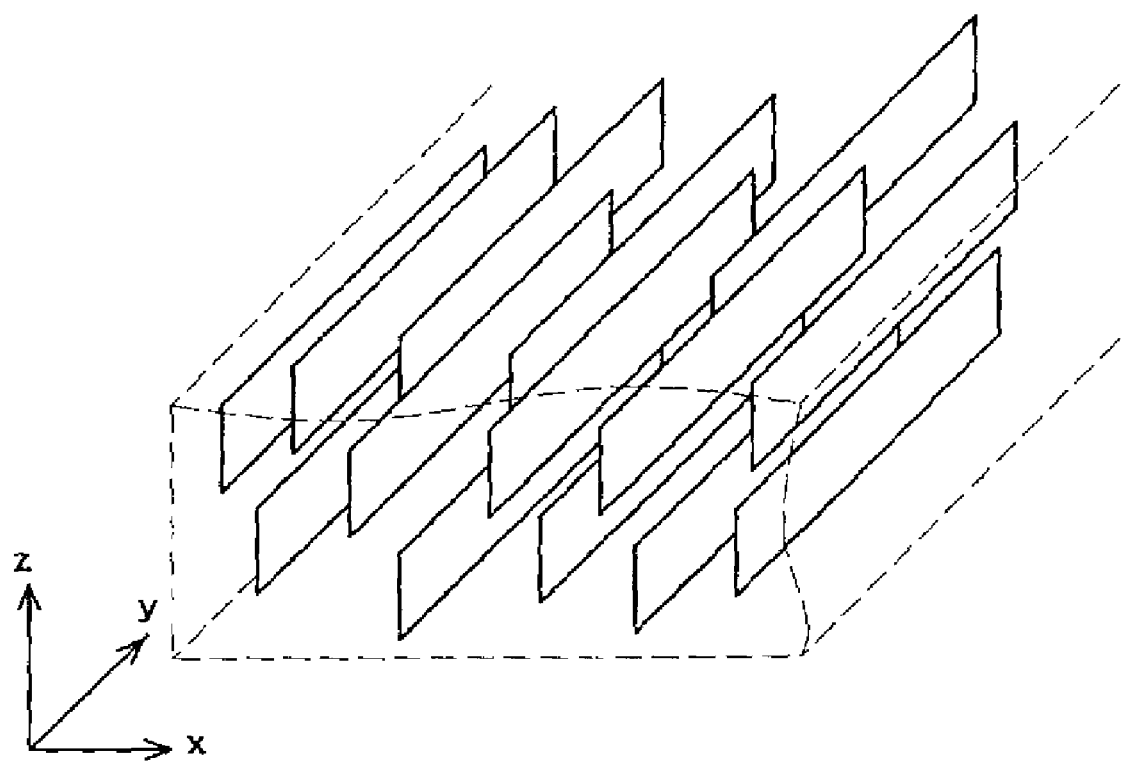
FIG. 4 is a perspective view that schematically shows the orientation status of the oligothiophene derivative in the semiconductor layer.

When employed as a semiconductor layer of the TFT, the oligothiophene derivative illustrated in FIG. 3 is preferably formed in order that the π conjugate planes are stacked in parallel as shown in FIG. 4. FIG. 4 shows one molecule of the oligothiophene derivative as a quadrangle in a strip shape as shown in FIG. 3C. In FIG. 4, the plane formed by the XY axes represents a plane parallel to the principle plane of the semiconductor layer, and the direction of the Z axis represents the direction of thickness of the semiconductor layer. Since the semiconductor layer thus formed has anisotropy of conductivity and an increased conductivity in the direction of the X axis, the source and the drain electrodes are preferably formed along with the direction of the X axis and facing each other.

Next, π electron conjugate system molecules (the second organic molecules), which modify the surfaces of the source and the drain electrodes 15 and 16 are described. As described in Background Art, in order to lower the connection resistance of the electrodes and the organic semiconductor, it is proposed to coat the electrodes with the monomolecular films that have high affinity to the organic molecules. The coating films conventionally proposed had their materials selected from the following perspectives: (1) a perspective of adjusting the gap between the ionization potential of the organic semiconductor and the work function of the electrode materials; and (2) a perspective of controlling the lipophilicity and the hydrophilicity. In contrast, the materials of the present invention are designed from a different perspective. That is, the materials are designed from the perspective in which the electrodes are preferably modified by the organic molecules including the π conjugate planes for the smooth charge transfer between the semiconductor layer and the electrode when an organic semiconductor, such as the one illustrated in FIGS. 3 and 4, containing π electron conjugate system molecules as its main component is employed.

FIGS. 5A to 5D show the second organic molecule employed in the First Example. Since the First Example employed Au as a material composing the source and the drain electrodes, a mercapto group (—SH) through which a tight bond with Au could be expected was employed as a bonding group. In the molecule in FIG. 5A, the naphthalene portion composes the π conjugate plane. In the molecules in FIGS. 5B and 5C, the porphyrin ring composes the π conjugate plane. In the molecule in FIG. 5D, the benzene ring composes the π conjugate plane. When the Au surfaces are reacted with these organic molecules, the Au atoms are bonded chemically to the sulfur atoms of their mercapto groups.

Hereinafter, the method of manufacturing the TFT 100b in the First Example is described. First, a Ni electrode in a predetermined shape (100 nm in thickness) was formed as the gate electrode 12 on a PET substrate (100 μm in thickness) by evaporation using a mask. Next, after applying an aqueous solution of polyvinyl alcohol by spin coating, it was dried to form the gate insulating layer 13 (500 nm in thickness). Subsequently, the source electrode 15 and the drain electrode 16 both are formed in predetermined shapes on the gate insulating layer by evaporation using a mask. Specifically an Au electrode (100 nm in thickness) was formed in order to have the channel length of 50 μm and the channel width of 500 μm.

Then, the substrate was immersed in a chloroform solution of the second organic molecule shown in FIG. 5 for one hour. The substrate was taken out after the immersion and it was cleansed with pure chloroform. After removing the unnecessary organic molecules (the organic molecules not bonded to the Au atoms) by the cleansing, it was dried to form an electrode modifying layer. This step chemically bonded the second organic molecules to the electrode surface. Further, after applying the chloroform solution of RR-poly(3-hexyl thiophene) by spin coating, it was dried to form the semiconductor layer 14 (500 nm in thickness). In the semiconductor layer 14 formed in this method, the π conjugate planes of RR-poly(3-hexyl thiophene) are disposed almost perpendicular to the surface of the substrate 11. They were also disposed almost parallel to the side walls of the source electrode 15 and the drain electrode 16 by providing orientation treatment, such as rubbing, to the surfaces of the gate insulating layer 13 (the surfaces on which the semiconductor layers are formed) between the source electrode 15 and the drain electrode 16 in advance.

The TFT 100b was formed in this way. Another TFT was formed as a Comparative Example by the same method except for not forming the electrode modifying layers.

Figure 6A:
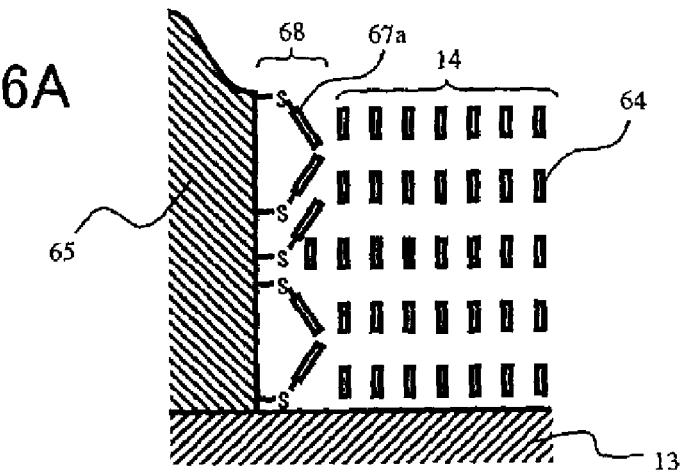
FIG. 6A is a cross-sectional view that schematically shows an example of the orientations of the first and the second organic molecules in the neighboring area of the channel region and the electrode.

FIG. 6 schematically show the state of the molecules in the part the electrode modifying layer and the channel region of the semiconductor layer 14 making contact with each other in each TFT fabricated in the above manner. In the bottom gate TFT 100b, the sides of the source and the drain electrodes are adjacent to the channel region, as shown in FIG. 6. On the side of the electrode, the electrode modifying layer 68 is formed. Although the molecular axes of the naphthalene portion are not always aligned in the identical direction as shown in FIG. 6A when the electrode is modified by the organic molecule of FIG. 5A, the π conjugate planes 67a indicated in rectangular form (shown in cross-section, forming planes extending in the direction of the front and the back sides of the page) are aligned at an almost constant angle (about 10°) to the surface of the Au electrode 65. Therefore, the angle formed by the π conjugate planes 64 of poly(3-hexyl thiophene) indicated in rectangular form (shown in cross-section, forming planes extending in the direction of the front and the back sides of the page) and the π conjugate planes 67a falls within a certain range of angles (about 10°).

Figure 5A:
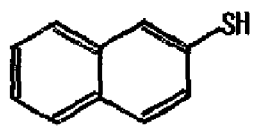
FIGS. 5A to 5D are chemical formulas that show an example of the organic molecule modifying the source and the drain electrodes.
Figure 5B:
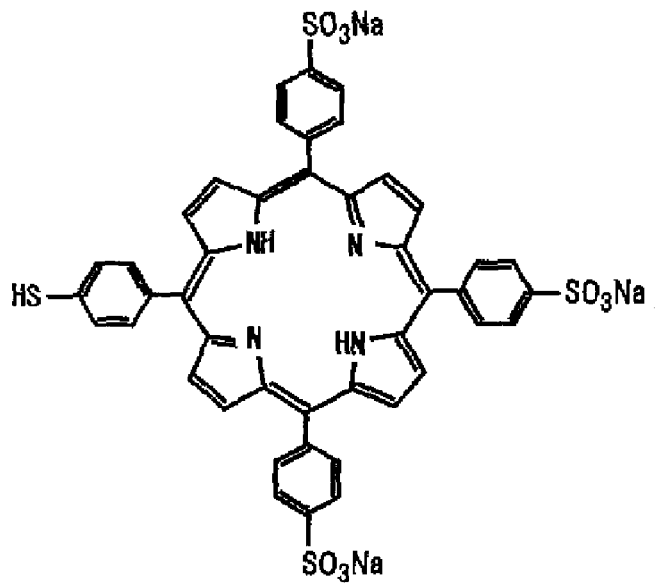
Figure 6B:
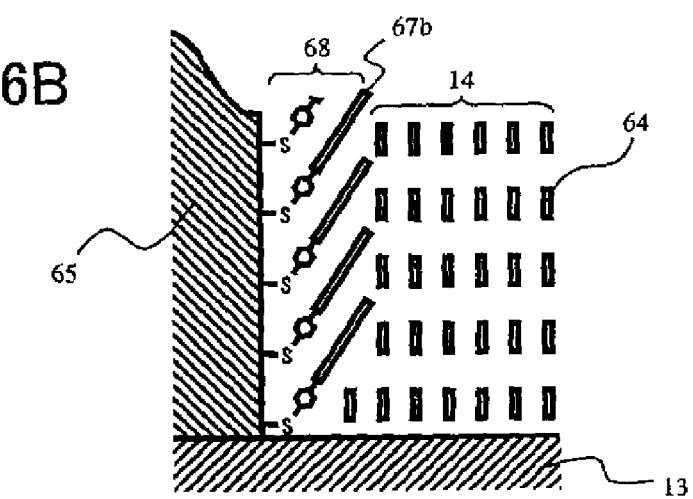
FIG. 6B is a cross-sectional view that schematically shows another example of the orientations of the first and the second organic molecules in the neighboring area of the channel region and the electrode.

When the electrode is modified by the organic molecule in FIG. 5B, since the porphyrin ring has a property of being stacked easily, they are bonded chemically with the molecular axes aligned to some extent as shown in FIG. 6B and the π conjugate planes 67b are aligned at an almost constant angle (about 10°) to the surface of the Au electrode 65. Therefore, any part of the π conjugate planes 64 of poly(3-hexyl thiophene) makes contact with the π conjugate planes 67b at almost the same angle (about 10°).

Figure 5C:
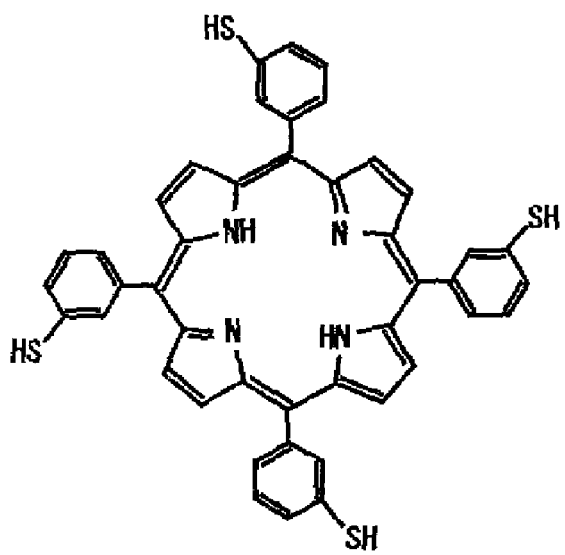
Figure 6C:
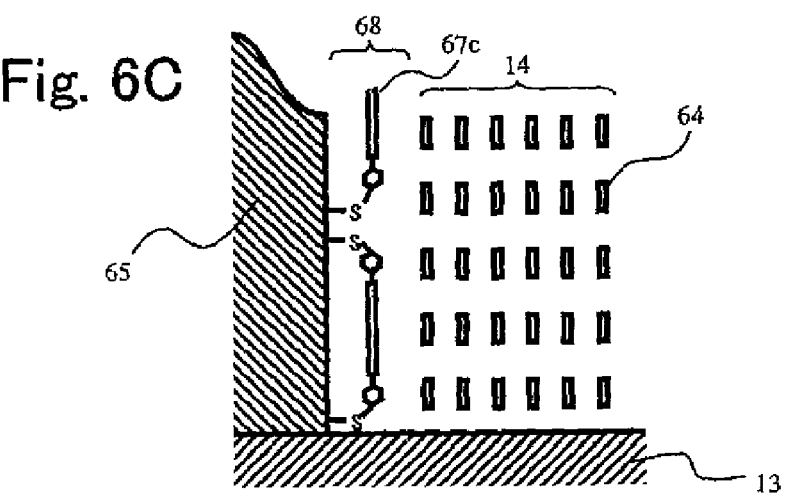
FIG. 6C is a cross-sectional view that schematically shows still another example of the orientations of the first and the second organic molecules in the neighboring area of the channel region and the electrode.

When the electrode is modified by the organic molecules in FIG. 5C, the organic molecules are bonded chemically to the surface of the Au electrode by four mercapto groups. Thus, as shown in FIG. 6C, the π conjugate planes 67c of the organic molecule in FIG. 5C are bonded chemically in parallel to the surface of the Au electrode 65 and in a constant density without overlapping each modifying group. Therefore, the π conjugate planes 64 of poly(3-hexyl thiophene) and the π conjugate planes 67c are almost in parallel, and they make contact with each other having their planes facing each other for the most part. Accordingly, any part of the π conjugate planes 64 of poly(3-hexyl thiophene) makes contact with the π conjugate planes 67c at almost the same angle (about 0°).

As shown in FIG. 6C, when three or more functional groups that are chemically bonded to the electrode surface exist on a π conjugate plane, the π conjugate plane can be aligned almost in parallel to the electrode surface. In this case, since the distance between the electrode surface and the π conjugate planes is close, the resistance between them can be reduced.

Figure 5D:
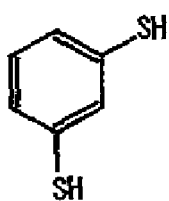

When the electrode is modified by the organic molecule in FIG. 5D, the organic molecule is bonded chemically to the Au electrode surface by the two mercapto groups. Thus, as shown in FIG. 6D, the n conjugate planes 67d of the organic molecule in FIG. 5D are aligned at an almost constant angle (about 0°) to the surface of the Au electrode. Therefore, any part of the π conjugate planes 64 of poly(3-hexyl thiophene) makes contact with the π conjugate planes 67d at almost the same angle (about 0°).

Driving voltages, their variations and carrier mobility of the thus fabricated TFTs of the present invention and the Comparative Example were evaluated. The driving voltage was evaluated with a source-drain voltage Vds by which a constant source-drain current Ids could be obtained under the state of "turned on". Specifically, a gate voltage (a gate-source voltage) Vgs=−40 V was defined as the state of "turned on", and the driving voltage was defined as a voltage value of Vds by which an Ids of 10 μA was obtained under the state. Practically, 64 samples of each TFT were measured to calculate the average value and the standard deviation. The carrier mobility was calculated by Ids obtained by measuring one typified sample out of each sample set under a fixed average value of the driving voltage at Vds when the Vgs was swept from +50 V to −80 V. Results of the evaluation of the driving voltages and carrier mobility are shown in Table 1.

TABLE 1

| | Driving Voltage (V) | | Carrier Mobility ($cm^2/V \cdot sec$) |
| --- | --- | --- | --- |
| | Average Value | Standard Deviation | |
| Comparative Example 1 (No Electrode Modification) | 83 | ±3.2 | 0.008 |
| Example 1a (Modified by the Compound of FIG. 5A) | 50 | ±2.3 | 0.015 |
| Example 1b (Modified by the Compound of FIG. 5B) | 38 | ±1.2 | 0.035 |
| Example 1c (Modified by the Compound of FIG. 5C) | 24 | ±0.5 | 0.051 |
| Example 1d (Modified by the Compound of FIG. 5D) | 49 | ±2.0 | 0.016 |

As shown in Table 1, the driving voltages, their variations and the carrier mobility were improved by modifying the surfaces of the source and the drain electrodes with the second organic molecules compared to the Comparative Example in which the electrode was not modified. The elements in which not only the angle formed by the π conjugate planes and the electrode surface but also the molecular axes of the organic molecules were aligned, as shown in FIG. 6B, developed better effects compared to the element of FIG. 6A, since the modifying molecules were disposed regularly. Better results were obtained by employing, as the organic molecules forming the electrode modifying layer, an organic molecule having the π conjugate system extended in two dimensions to some extent, such as the porphyrin rings shown in FIGS. 5B and 5C.

When the π conjugate planes of the modifying molecules composing the electrode modifying layer and the π conjugate planes of the molecules composing the semiconductor layer 14 were almost in parallel, as shown in FIG. 6C, even better effects were obtained. In the configuration shown in FIG. 6C, since the π conjugate planes of the porphyrin rings become parallel to the electrode surface and thus the overlaps of the modifying molecules mostly are excluded by forming a plurality of chemical bonds by the modifying molecules composing the electrode modifying layer and the electrode. Therefore, it is considered that the density of the modifying electrodes on the electrode surface becomes uniform and thus it exhibits a large effect on reducing the variations.

Second Example

An example of manufacturing the TFT 100d shown in FIG. 1D is described below. In this Example, the components except the electrode modifying layer were formed by the same materials as the First Example.

Figure 7A:
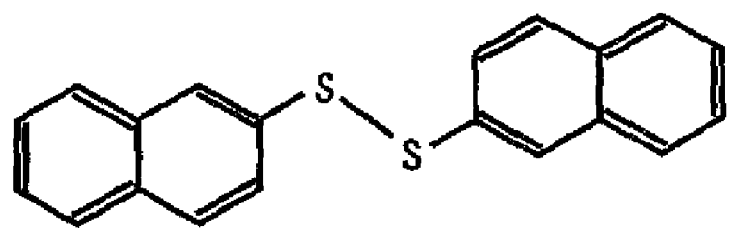
FIGS. 7A and 7B are chemical formulas that show another example of the organic molecule modifying the source and the drain electrodes.
Figure 7B:
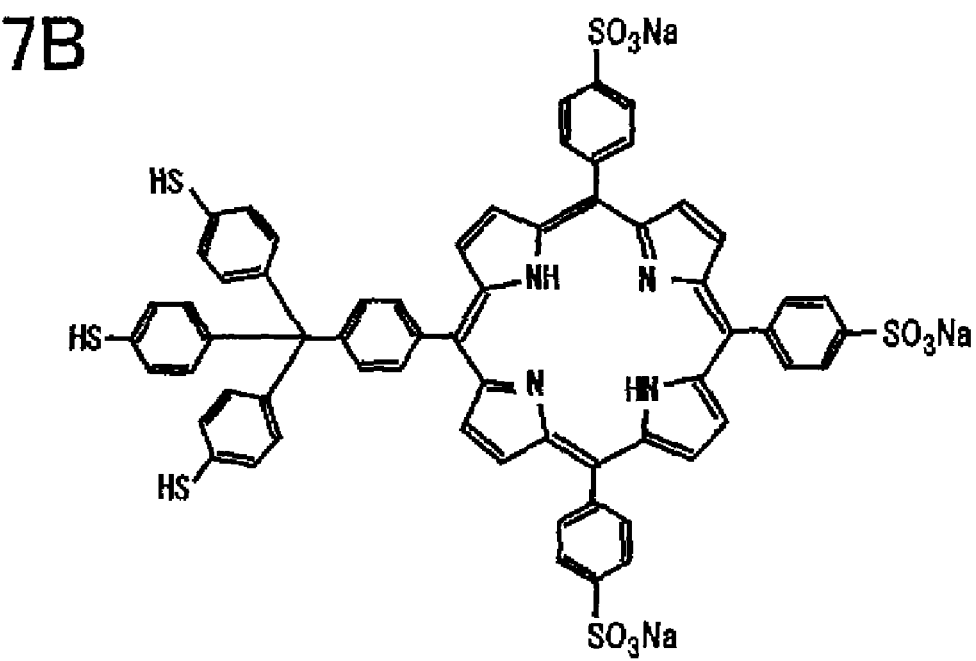

In this example, an electrode modifying layer was formed by the organic molecules shown in FIG. 7A or 7B. Since the source and the drain electrodes were formed by Au in this example as well, disulfide (FIG. 7A) and a compound having mercapto groups (FIG. 7B) were employed for organic molecules through which a tight bond on the Au electrode surface could be expected. The naphthalene portions in the molecule of FIG. 7A and the porphyrin rings in the molecule of FIG. 7B are the main π conjugate planes. In the molecule of FIGS. 7A, S-S linkage is cut and the sulfur atoms and the Au atoms are bonded chemically. In the molecule of FIG. 7B, the sulfur atoms in the mercapto groups and the Au atoms are bonded chemically.

Hereinafter, the method of manufacturing the TFT 100d in the Second Example is described. First, the source electrode 15 and the drain electrode 16 both in predetermined shapes were formed on a PET substrate (100 μm in thickness) by evaporation using a mask. Specifically, an Au electrode (100 nm in thickness) was formed by evaporation using a mask in order to have the channel length of 50 μm and the channel width of 500 μm. After that, the substrate was immersed in a chloroform solution of the organic molecule shown in FIG. 7 for one hour. The substrate was taken out after the immersion and it was cleansed with pure chloroform. After removing the unnecessary organic molecules (the organic molecules not bonded to the Au atoms) by the cleansing, it was dried and thus an electrode modifying layer was formed.

Next, after applying the chloroform solution of RR-poly (3-hexyl thiophene) by spin coating, it was dried to form the semiconductor layer 14 (250 nm in thickness). Subsequently, after applying an aqueous solution of polyvinyl alcohol by spin coating, it was dried to form the gate insulating layer 13 (500 nm in thickness). Then, a Ni electrode (100 nm in thickness) was formed as the gate electrode 12 by evaporation using a mask. The TFT 100d was formed in this way. Another TFT also was formed as a Comparative Example by the same method except for not forming the electrode modifying layers.

FIG. 8 schematically show the state of the molecules in the part the electrode modifying layer and the channel region of the semiconductor layer 14 making contact with each other in each TFT fabricated in the above manner. In the top gate TFT 100d of FIG. 1D, mainly the top face of the electrode makes contact with the channel region, as shown in FIG. 8.

Figure 8A:
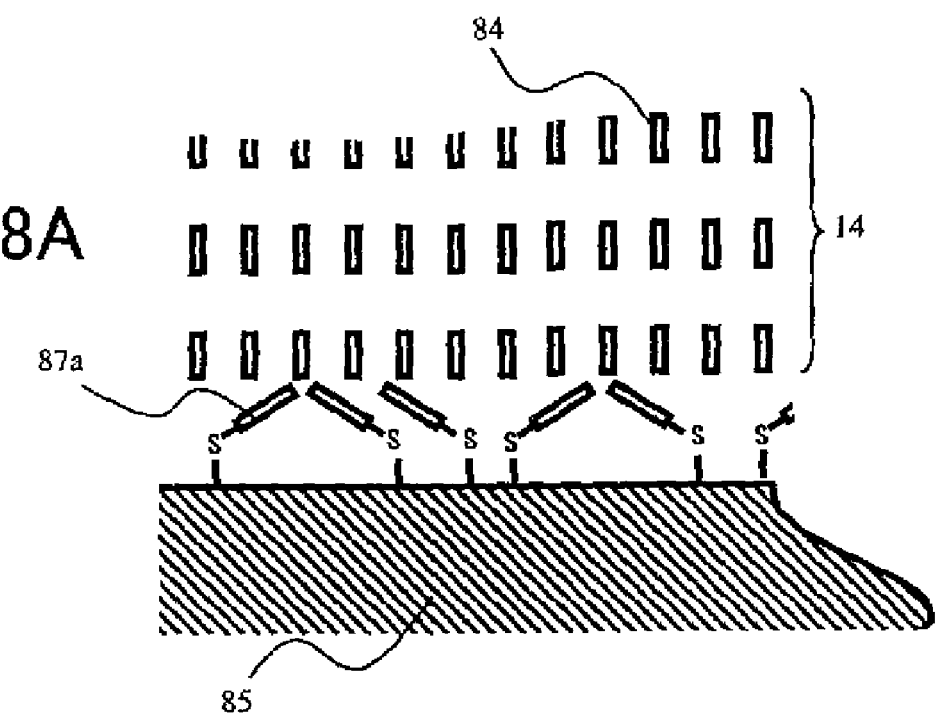
FIGS. 8A and 8B are cross-sectional views that schematically show the orientation status of the organic molecules in the neighboring area of the electrode.

Although the molecular axes of the naphthalene portion are not always aligned in the identical direction as shown in FIG. 8A when the electrode is modified by the organic molecule of FIG. 7A, the π conjugate planes 87a (shown in cross-section, forming planes extending in the direction of the front and the back sides of the page) are aligned at an almost constant angle (about 10°) to the surface of the Au electrode 85. Therefore, any part of the π conjugate planes 87a makes contact with the π conjugate planes 84 of poly(3-hexyl thiophene) (shown in cross-section, forming planes extending in the direction of the front and the back sides of the page) at almost the same angle (about 80°).

Figure 8B:
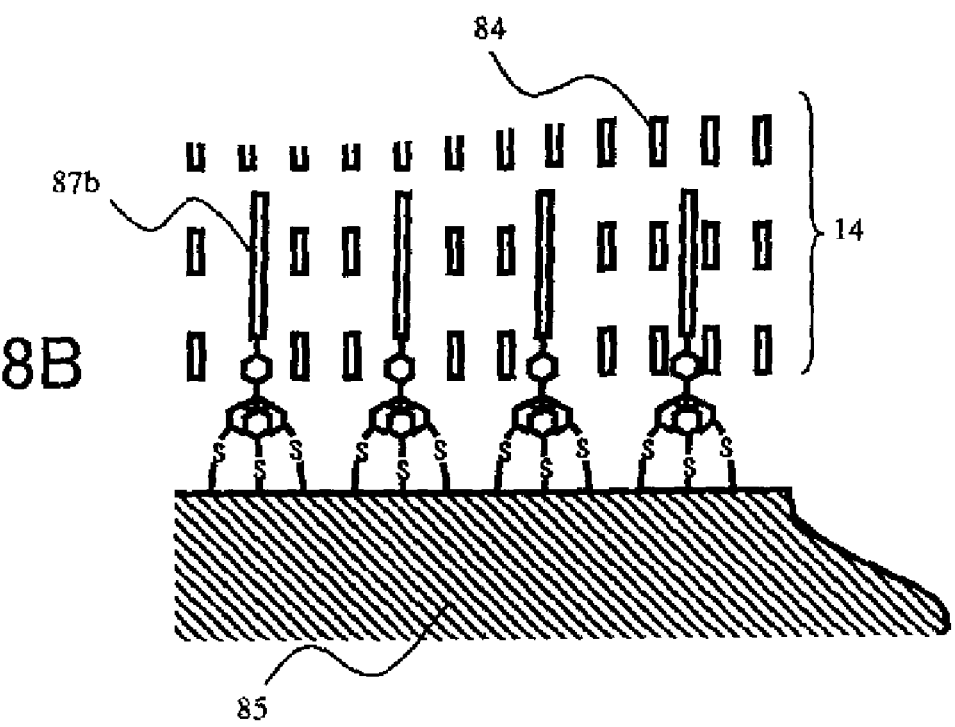

The organic molecules in FIG. 7B are bonded to the electrode surface by three bonding groups, and their porphyrin rings (the π conjugate planes 87b) are almost perpendicular to the electrode surface. By the self-assembly due to steric barrier among the porphyrin rings, the organic molecules of FIG. 7B are bonded to the electrode surface with the molecular axes aligned as shown in FIG. 8B. Therefore, the π conjugate planes 84 of poly(3-hexyl thiophene) and the π conjugate planes 87b are almost in parallel for the most part.

Driving voltages, their variations and carrier mobility of the thus fabricated TFTs of the present invention and the Comparative Example were evaluated in a similar manner to the First Example. Results of the evaluation of the driving voltages and carrier mobility are shown in Table 2.

TABLE 2

|  | Driving Voltage (V) | | Carrier Mobility ($cm^2/V \cdot sec$) |
| --- | --- | --- | --- |
|  | Average Value | Standard Deviation |  |
| Comparative Example 2 (No Electrode Modification) | 86 | ±3.0 | 0.006 |
| Example 2a (Modified by the Compound of FIG. 7A) | 64 | ±2.1 | 0.010 |
| Example 2b (Modified by the Compound of FIG. 7B) | 29 | ±0.7 | 0.045 |

As shown in Table 2, any of the driving voltages, their variations and the carrier mobility was improved by modifying the surfaces of the source and the drain electrodes with the second organic molecules compared to the Comparative Example in which the electrode was not modified.

In addition, since the elements of FIG. 5B had the molecular axes of the second organic molecules better aligned and thus their second organic molecules were disposed regularly compared to the element of FIG. 8A, better effects were obtained. Better results were obtained by employing a second organic molecule having the π conjugate system extended in two dimensions to some extent, such as the porphyrin rings shown in FIG. 7B. Still in addition, since the π conjugate planes of the porphyrin rings are disposed perpendicular to the electrode surface and the π conjugate planes 84 face the π conjugate planes 87b of the modifying molecules almost in parallel in the elements of FIG. 7B, even better effects were obtained.

Third Example

In this example, a TFT in which the π electron conjugate system molecules bonded to the electrode surface are insulated by the cyclic molecules is described.

In this example, TFT 100d was fabricated in the same manner as the Second Example except for the organic molecules composing the semiconductor layer 14 and the electrode modifying layer are different. The semiconductor layer 14 was formed of pentacene. The organic molecules composing the electrode modifying layer are described later.

Figure 9A:
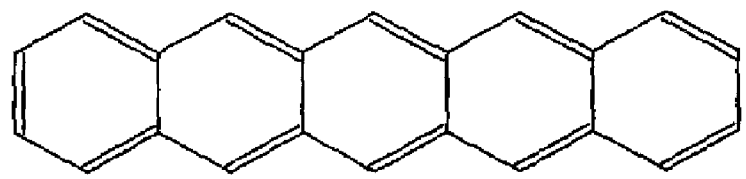
FIG. 9A is a drawing that shows the chemical formula of pentacene employed for the semiconductor layer.
Figure 9B:
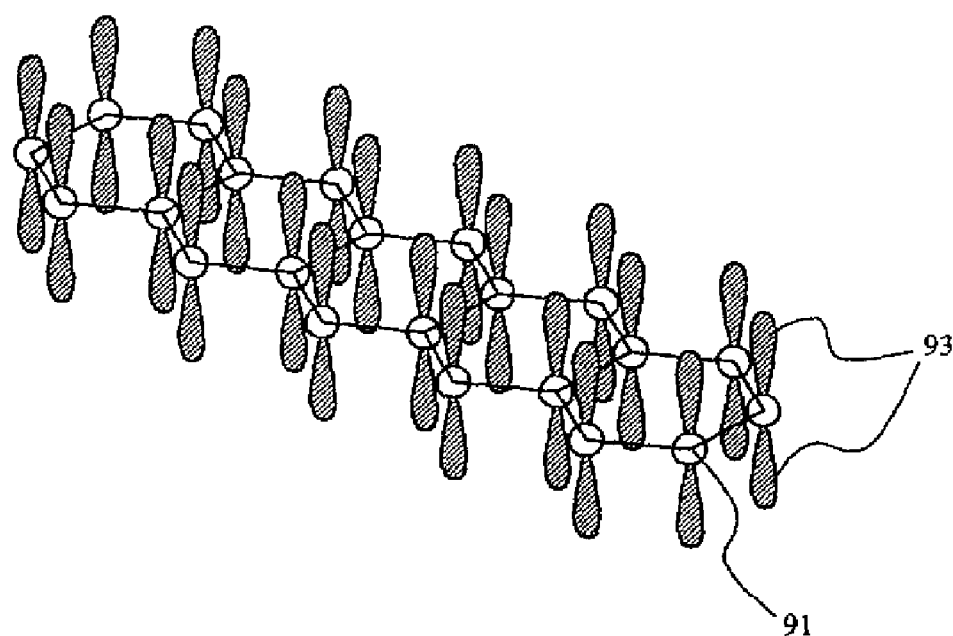
FIG. 9B is a drawing that shows the σ bond and the π electron cloud of the same and FIG. 9C is a perspective view that schematically shows the π conjugate plane of the same.
Figure 9C:
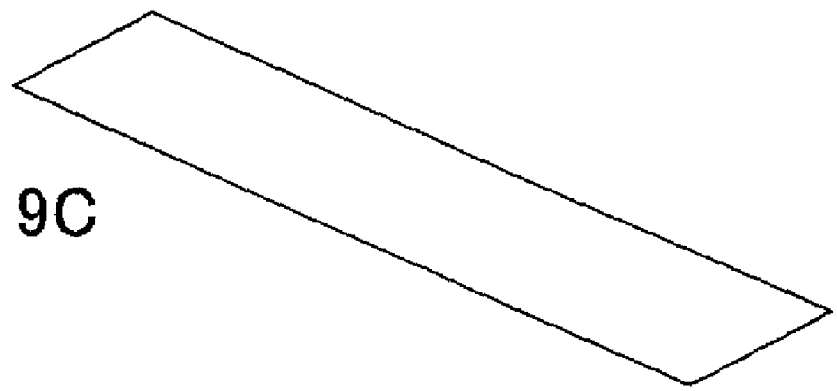

Pentacene composing the semiconductor layer 14 is described as follows. FIG. 9A shows a structural formula of pentacene. FIG. 9B is a perspective view that shows the σ bond and the π electron cloud of pentacene. FIG. 9C is a perspective view that schematically shows the π conjugate plane of pentacene disposed in the direction of FIG. 9B.

As shown in FIG. 9A, pentacene has a developed π conjugate system composed of repeatedly bonded six-membered rings having a plurality of double bonds. FIG. 9A does not show the hydrogen atoms. As shown in FIG. 9B, a π electron cloud 93 exists in pentacene, in the perpendicular direction to faces of each six-membered ring composed of carbon atoms 91. Since each six-membered ring is present in the same plane in pentacene, the vectors showing the distributed direction of the π electron cloud 93 are aligned uniformly in the direction perpendicular to the quadrangle shown in FIG. 9C.

Figure 10:
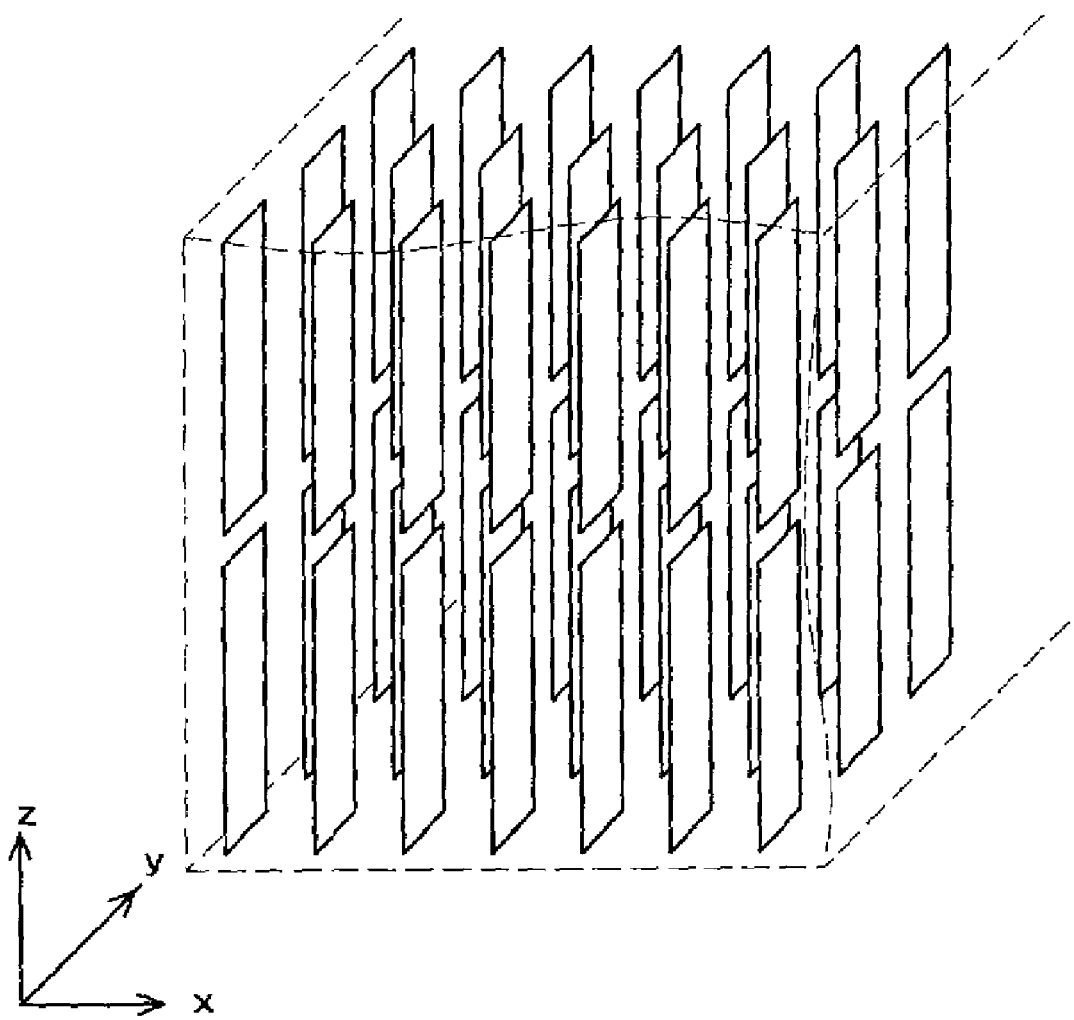
FIG. 10 is a perspective view that schematically shows the orientation status of pentacene in the semiconductor layer.

When composing a semiconductor layer of the TFT, pentacene is used preferably in order that the π conjugate planes are stacked in parallel as shown in FIG. 10. Similar to FIG. 9C, FIG. 10 shows one molecule of pentacene as a quadrangle in a strip shape. In FIG. 10, the plane formed by the XY axes represents a plane parallel to the principle plane of the semiconductor layer, and the direction of the Z axis represents the direction of thickness of the semiconductor layer. The semiconductor layer formed as shown in FIG. 10 has anisotropy of conductivity and an increased conductivity in the direction of the X axis. For this reason, the source and the drain electrodes preferably are formed along with the direction of the X axis and facing each other.

Figure 11A:
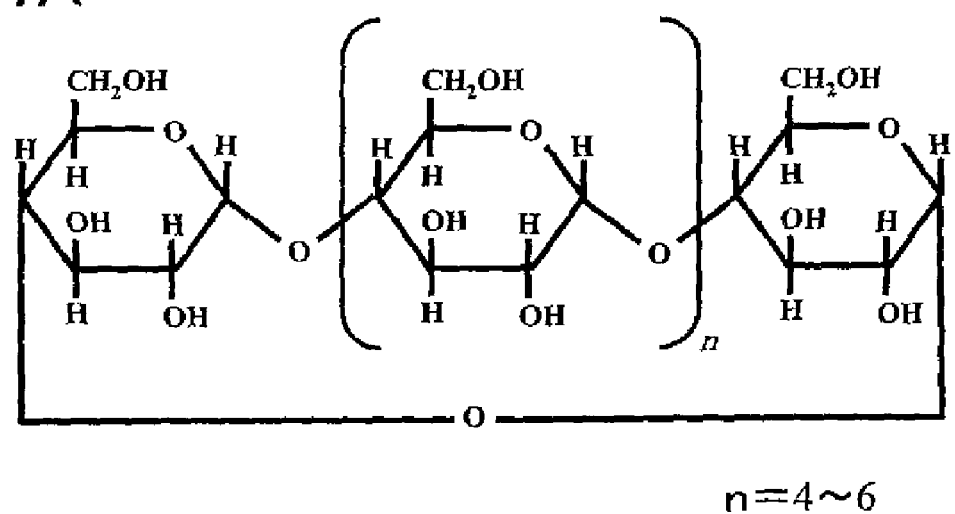
FIG. 11A is a drawing that shows the chemical formula of cyclodextrin and FIG. 11B is a drawing that schematically shows its shape.
Figure 11B:
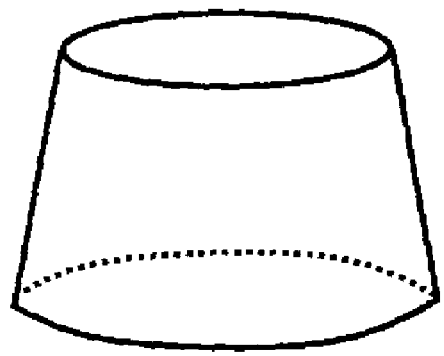

Next, the organic molecules composing the electrode modifying layer are described. The electrode modifying layer was formed by π electron conjugate system molecules having the conjugated π electrons composing the π conjugate planes and cyclic molecules insulating the π electron conjugate system molecules. FIG. 11A shows the structure of the employed cyclic molecule. The cyclodextrin represented by the general formula of FIG. 11A is a cyclic oligomer of glucose, and the size of the cyclic structure varies depending on the number of glucose. Among cyclodextrin, α-cyclodextrin of n=4, β-cyclodextrin of n=5 and γ-cyclodextrin of n=6 are common, and a suitable one can be selected according to the size of molecule to be insulated. The figures mentioned in the description below also may indicate schematically cyclodextrin as shown in FIG. 11B.

Figure 12A:
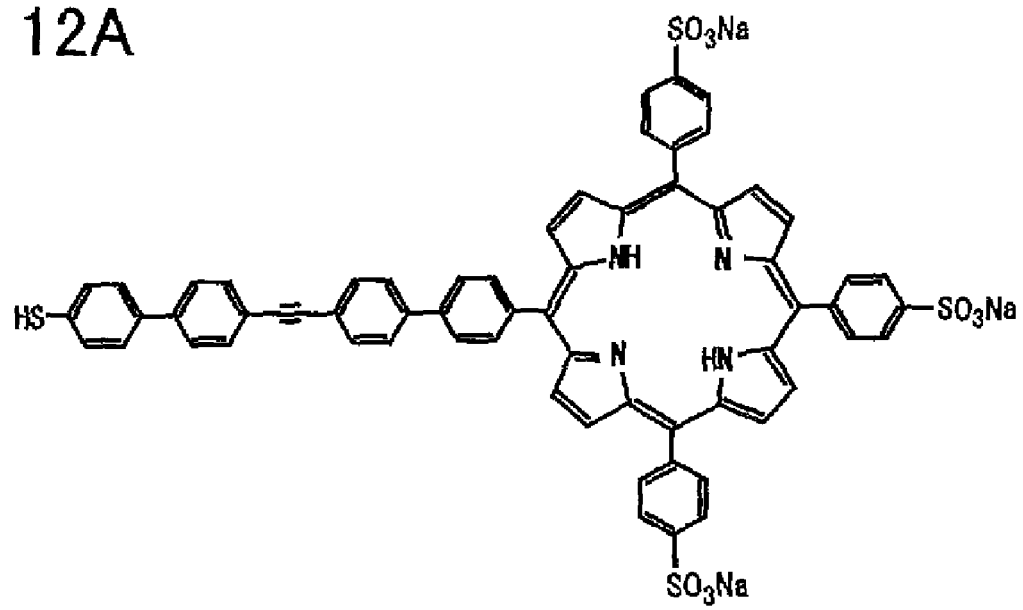
FIG. 12A is a chemical formula that shows the organic molecule modifying the source and the drain electrodes of the Comparative Example.

FIG. 12A shows the organic molecule bonded to the surfaces of the source electrode 15 and the drain electrode 16. Since in the Third Example the source and the drain electrodes are formed by Au as well, a mercapto group through which a tight bond with Au could be expected was employed as a bonding group.

Figure 12B:
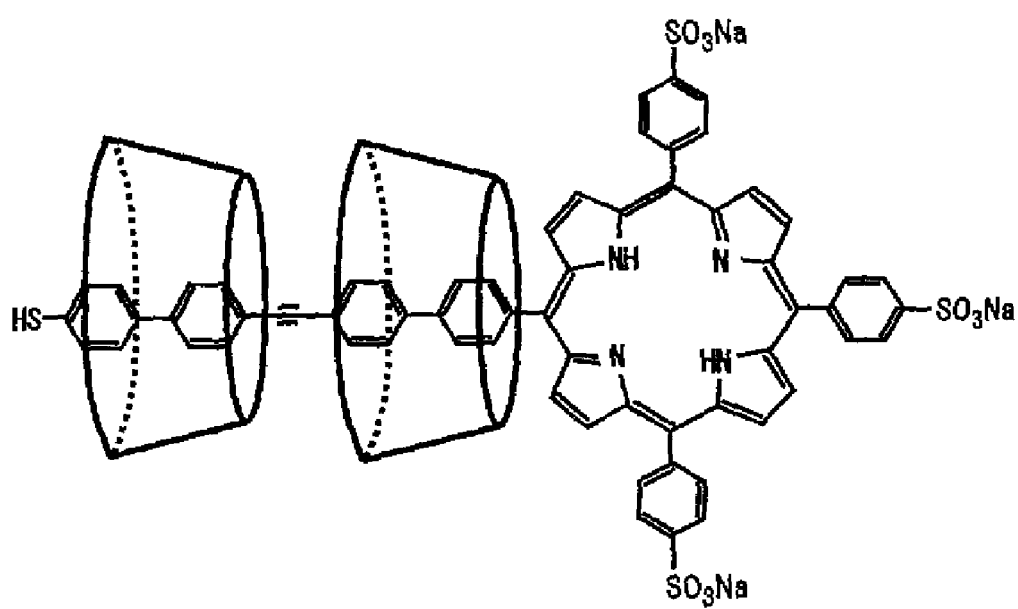
FIG. 12B is a chemical formula that shows the organic molecule modifying the source and the drain electrodes of the Example.

The inside of the cyclic structure of cyclodextrin shown in FIG. 11A is hydrophobic. Thus, when the second organic molecules shown in FIG. 12A are mixed with cyclodextrin (β-cyclodextrin was employed in this Example) in an aqueous solvent, the molecular chains of the second organic molecules are insulated by cyclodextrin as shown in FIG. 12B. In the organic molecule of FIG. 12B, the porphyrin ring composes the main π conjugate planes. When the organic molecule of FIG. 12B and the surface of the Au electrode are reacted, the sulfur atoms of the mercapto group and the Au atoms are bonded chemically.

Hereinafter, the method of manufacturing the TFT 100d is described. First, the source electrode 15 and the drain electrode 16 both in predetermined shapes were formed on the PET substrate (100 μm in thickness) by evaporation using a mask. Specifically, an Au electrode (100 nm in thickness) was formed by masked evaporation in order to have the channel length of 50 μm and the channel width of 500 μm. After that, the substrate was immersed in an aqueous solution of the organic molecule shown in FIG. 12B for one hour. The substrate was taken out after the immersion and it was cleansed with pure water. After removing the unnecessary organic molecules (the organic molecules not bonded to the Au atoms) by the cleansing, it was dried and thus the electrode surfaces were modified by the second organic molecules.

Next, the semiconductor layer 14 (50 nm in thickness) made of pentacene was formed by evaporation using a mask. Evaporation was carried out under a condition of a substrate temperature of 90° C. and an evaporation rate of 0.1 nm/second. By this method, pentacene was oriented to make the π conjugate planes are almost perpendicular to the surface of the substrate.

Then, after applying an aqueous solution of polyvinyl alcohol by spin coating, it was dried to form the gate insulating layer 13 (500 nm in thickness). Subsequently, a Ni electrode (100 nm in thickness) was formed as the gate electrode 12 on the PET substrate (100 μm in thickness) by evaporation using a mask. The TFT 100d was formed in this way. Another TFT also was formed as a Comparative Example by the same method except for forming the electrode modifying layers only by the organic molecules (the organic molecules of FIG. 12A) not insulated by the cyclic molecules.

Figure 13A:
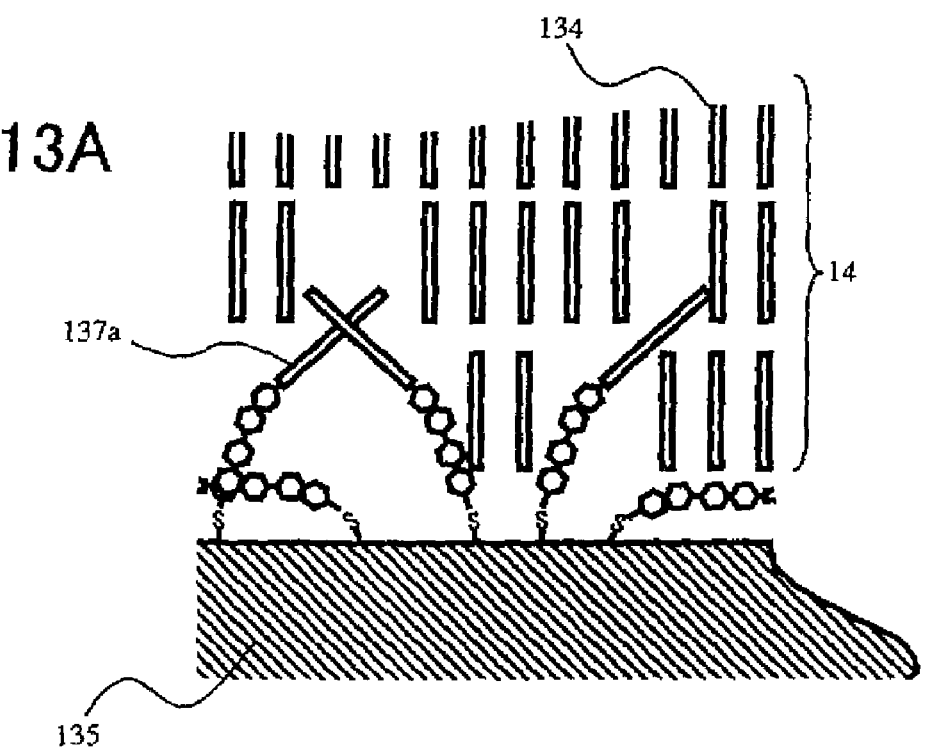
FIG. 13A is a cross-sectional view that schematically shows the orientation status of the organic molecules in the neighboring area of the electrode of the Comparative Example.

FIG. 13 schematically show the state of the molecules in the part the electrode modifying layer and the channel region of the semiconductor layer 14 making contact with each other in each TFT prepared in the above manner. In the TFT 100d of FIG. 1D, mainly the top face of the electrode makes contact with the channel region, as shown in FIG. 13.

Figure 13B:
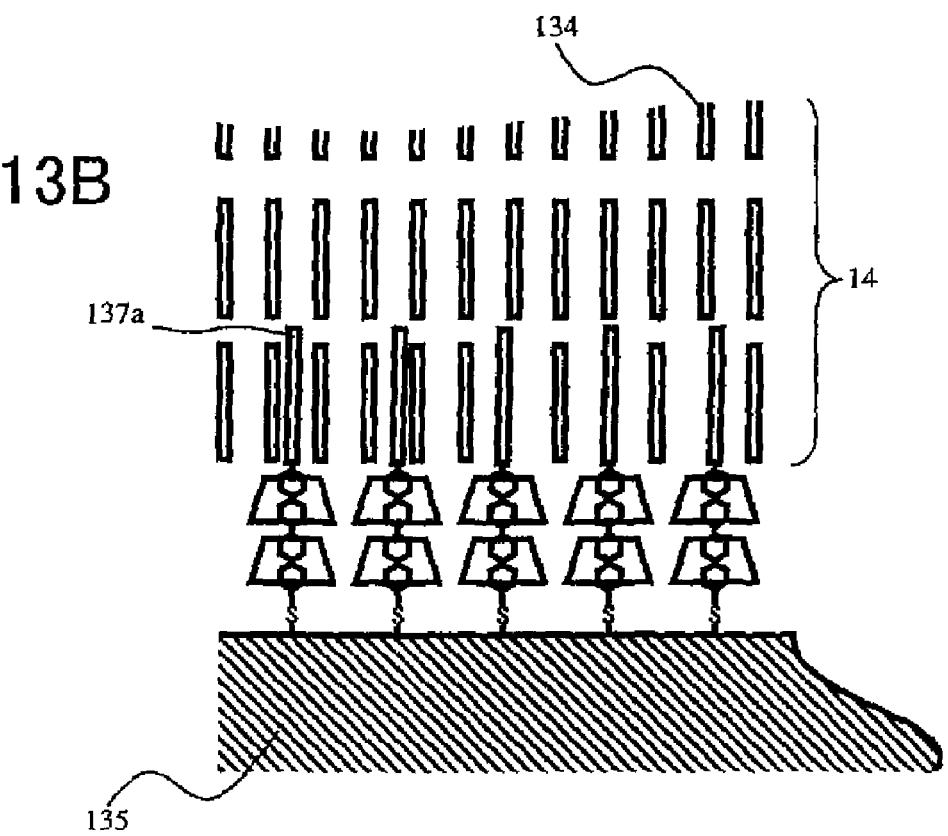
FIG. 13B is a cross-sectional view that schematically shows the orientation status of the organic molecules in the neighboring area of the electrode of the Example.

When the electrode is modified by the organic molecule of FIG. 12A, since the main chains present between the π conjugate planes of the organic molecules and the electrode are long, it is considered that the organic molecules have low self-support and bend in the middle. Therefore, the π conjugate planes 137a (shown in cross-section, forming planes extending in the direction of the front and the back sides of the page) are considered to be random relative to the surface of the Au electrode 135. In contrast, since the linearity of the molecular chains is improved by being insulated by the cyclodextrin when the electrode is modified by the organic molecules of FIG. 12B, the porphyrin rings (the π conjugate planes 137a) become perpendicular to the electrode surface. As a result, as shown in FIG. 13B, the organic molecules are bonded chemically to the electrode with their molecular axes aligned. Accordingly, the π conjugate planes 134 of pentacene and the π conjugate planes 137a are, for the most part, aligned almost in parallel while making contact with each other. That is, in a case of FIG. 13B, the angle formed by the π conjugate planes 137a and the π conjugate planes 134 is equal to or less than 30°. In addition, since cyclodextrin limits approach and overlap among porphyrin, it becomes possible to uniform the density of the organic molecules bonding to the electrode.

Driving voltages, their variations and carrier mobility of the thus fabricated TFTs were evaluated in a similar manner to the First Example. Results of the evaluation of the driving voltages and carrier mobility are shown in Table 3.

TABLE 3

| | Driving Voltage (V) | | Carrier |
| --- | --- | --- | --- |
| | Average Value | Standard Deviation | Mobility ($cm^2$/V · sec) |
| Comparative Example 3 (Modified by the Compound of FIG. 12A) | 63 | ±2.8 | 0.08 |
| Example 3 (Modified by the Compound of FIG. 12B) | 15 | ±0.5 | 0.73 |

As shown in Table 3, any of the driving voltages, their variations and the carrier mobility was excellent in the TFT of the present invention compared to that of the Comparative Example. This is because in the TFT of the Third Example, as shown in FIG. 13B, the π conjugate planes of the porphyrin rings were disposed perpendicular to the electrode surface, the π conjugate planes of the π electron conjugate system molecules of the semiconductor layer faced the π conjugate planes of the modifying molecules in parallel, and the density of the modifying molecules on the electrode surface was uniformed.

Although RR-poly(3-hexyl thiophene) or pentacene was employed as the π electron conjugate system molecules composing the semiconductor layer in the above examples, the present invention is not limited to this. In other words, the effects of the present invention are exhibited because the π conjugate planes of the π electron conjugate system molecules bonded to the electrode surface are mostly aligned to a predetermined angle relative to the electrode surface, so that the same effects are obtained when the semiconductor layer is composed of other π electron conjugate system molecules.

For example, a derivative of thiophene series molecules, such as polythiophene introducing side chains different from those of the polythiophene derivatives, or polythiophene introducing a modifying group at the ends may be employed. A derivative of acetylene series molecules, such as polyacetylene or polyphenylacetylene, also may be employed. Condensed ring aromatic hydrocarbon and its derivatives, for example a derivative of acene series molecules, such as tetracene and hexacene, and a derivative of phene series molecules, such as phenanthrene and chrysene, also may be employed. In addition, a derivative of pyrrole series molecules, such as polypyrrole and polyalkylpyrrole, and a derivative of phenylene series molecules, such as oligophenylene and polyphenylene, also may be employed. A derivative of copolymers obtained by combining with these molecules themselves, vinyl groups, ethynyl groups and the like also may be employed. Among these, organic molecules that have the π conjugate planes of each molecule stacked almost in parallel when formed as a film are preferred. Still in addition, organic molecules in which the π conjugate plane making contact with the electrode surface in the channel region is easily aligned also are preferred. As such organic molecules, organic molecules having π conjugate planes extended in two dimensions are preferred, and for example, organic molecules having a condensed ring or porphyrin are preferable. The organic molecules having a condensed ring are organic molecules having a ring in which two or more rings (five-membered ring or six-membered ring, for example) are condensed, and the derivatives of acene and phene series molecules mentioned above fall within those.

In the examples above, since Au electrodes were employed for the source and the drain electrodes, the mercapto group was employed as the bonding group for the modifying organic molecules. However, the combinations of the electrode materials and the bonding groups bonded to the electrode are not limited to above-mentioned combination. In order to achieve a tight bond, it is preferred to select the combination of the electrode material and the bonding group according to the classification of HSAB (Hard and Soft Acids and Base) Principle by Peason et al. Specifically, preferred combinations are either combinations of a hard acid (such as $Ca^{2+}$, $Mg^{2+}$ and $Al^{3+}$) and a hard base (such as ROH, $R_2O$ and $RNH_2$), or combinations of a soft acid (such as $Cu^+$, $Ag^+$, $Au^+$ and $Pt^+$) and a soft base (such as $R_2S$, RSH and $R_3P$). When employing these combinations, the electrode surfaces include a metallic element of the hard acid or the soft acid, and the second organic molecules are provided with a substituent of the hard base or the soft base. Typical combinations may be, for example, a combination of Au and a mercapto group (Au/—SH), a combination of Pt and a mercapto group (Pt/—SH) and a combination of calcium and a hydroxide group (Ca/—OH). In addition, since the elements classified in the same group in periodic table show similar properties among the ones selected as above, it is possible to replace the sulfur atoms with Se or Te, for example. In a case of a multilayer electrode, it is sufficient to form the surface of the top layer of the electrode with these elements.

Further in addition, although the organic molecules shown in FIGS. 5A to 5D, 7A, 7B and 12B were employed as the organic molecules (the second organic molecule) composing the electrode modifying layer in the Examples, the present invention is not limited to them. For example, a derivative of thiophene series molecules, such as polythiophene introducing side chains different from those of the polythiophene derivatives, or polythiophene introducing a modifying group at the ends may be employed. A derivative of acetylene series molecules, such as polyacetylene or polyphenylacetylene, also may be employed. Condensed ring aromatic hydrocarbon and its derivatives, for example a derivative of acene series molecules, such as tetracene and hexacene, and a derivative of phene series molecules, such as phenanthrene and chrysene, also may be employed. In addition, a derivative of pyrrole series molecules, such as polypyrrole and polyalkylpyrrole, and a derivative of phenylene series molecules, such as oligophenylene and polyphenylene, also may be employed. A derivative of copolymers obtained by combining with these molecules themselves, vinyl groups, ethynyl groups and the like also may be employed.

It is preferable that the organic molecules composing the electrode modifying layer have their main π conjugate system extended in two dimensions. Since the π conjugate planes of such molecules easily face the π conjugate planes of the organic molecules composing the semiconductor layer 14, the connection resistance between the electrode modifying layer and the semiconductor layer 14 and the variations can be reduced. Although the molecular structures other than the part of the main π conjugate system are not limited to the structures exemplified above, it is preferable that a main π conjugate plane and a bonding group are connected by a π conjugate system. As shown in FIG. 14, porphyrin and phthalocyanine derivatives may form a complex by including a metal in the center.

The three examples above described a method of manufacturing the bottom contact TFTs by the first manufacturing method of the present invention. A top contact TFT (the TFTs in FIGS. 1A and 1C, for example) may be manufactured similarly by the second manufacturing method of the present invention. In such a case, after forming the semiconductor layer 14, the electrode modifying layer is formed on the surface thereof. After that, the source electrode 15 and the drain electrode 16 are formed on the electrode modifying layer. The organic molecules of the electrode modifying layer and the atoms composing the electrode are reacted when the electrodes are formed, and thus the organic molecules and the electrode are bonded chemically. The other layers can be formed by known methods.

A top contact TFT also can be formed by the third manufacturing method of the present invention. In this case, firstly, the source electrode 15 and the drain electrode 16 are formed on a substrate intended for transfer. Next, the surfaces of the source electrode 15 and the drain electrode 16 are modified by the second organic molecules. The method of modifying the electrodes is the same as the first manufacturing method. Then, after the source electrode 15 and the drain electrode 16 modified by the second organic molecules are attached to the semiconductor layer 14, the substrate for transfer is peeled off. In this way, source electrode 15 and the drain electrode 16 are transferred on the semiconductor layer 14, and thus source electrode 15 and the drain electrode 16 become adjacent to the semiconductor layer 14 via the electrode modifying layer formed on the surface thereof. The other layers can be formed by well-known methods.

The substrate for transfer employed in the third manufacturing method is preferably a flexible substrate, such as one made of resin. In addition, for easier transfer, it is allowed to help the peeling of the substrate for transfer from the electrodes by applying a release agent and the like on the surface of the substrate.

In addition, the TFTs in FIGS. 2A and 2B may be fabricated by the methods described above. For example, the TFT in FIG. 2B may be formed by forming the semiconductor layer 14 up to about half of the thickness, followed by forming layers in the order of the gate insulating layer 13, the gate electrode 12 and the gate insulating layer 13, and then forming the rest of the semiconductor layer 14 and the drain electrode 16.

Embodiment 2

In the Embodiment 2, an active matrix display, a wireless ID tag and portable apparatuses are described as examples of the apparatus having the TFT of the present invention described in the Embodiment 1.

As an example of the active matrix display, a display using an organic EL for the display screen is described. A partially exploded perspective view that schematically shows the configuration of the display is shown in FIG. 15.

The display shown in FIG. 15 is provided with a driving circuit 150 disposed in an array on a plastic substrate 151. The driving circuit 150 includes the TFT of the present invention and is connected to a pixel electrode. An organic EL layer 152, a transparent electrode 153 and a protective film 154 are disposed on the driving circuit 150. The organic EL layer 152 has a structure in which a plurality of layers, such as an electron transport layer, a luminescent layer and a positive hole transport layer, are stacked. Source electrode wires 155 and gate electrode wires 156 connected to the electrodes of each TFT are connected to a controlling circuit (not shown), respectively.

Figure 16:
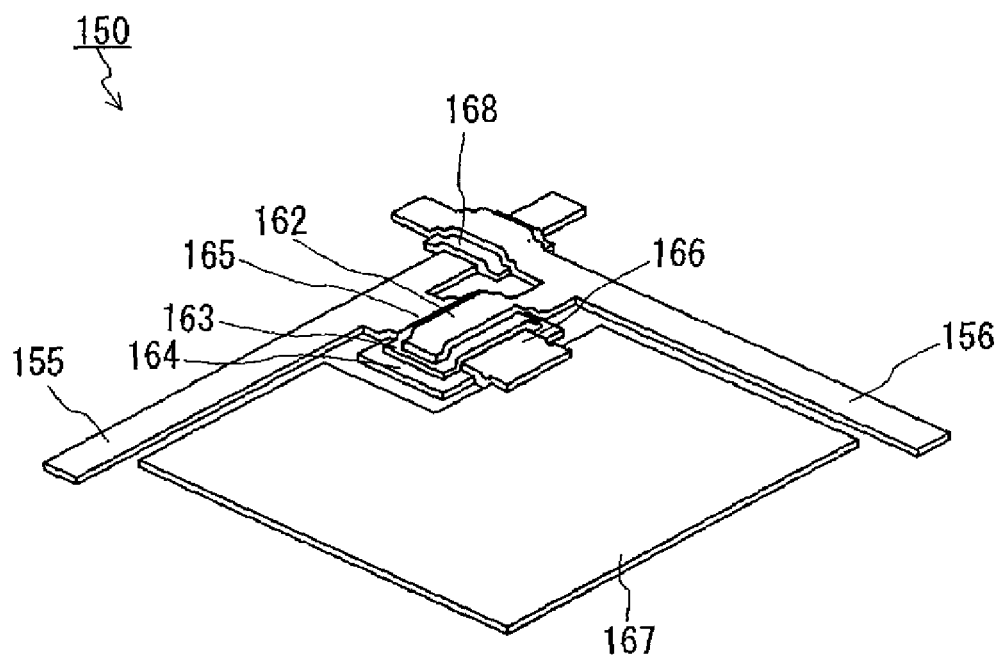
FIG. 16 is a perspective view that schematically shows the configuration of the driving circuit and its neighboring area in the display shown in FIG. 15.

FIG. 16 shows an enlarged view of an example of the driving circuit 150 and the neighboring area. The structure of the TFT shown in FIG. 16 is basically the same as the structure shown in FIG. 1C. That is, in the TFT shown in FIG. 16, a semiconductor layer 164, a source electrode 165 and a drain electrode 166, a gate insulating layer 163 and a gate electrode 162 are stacked on a substrate. As shown in FIG. 16, the drain electrode 166 is connected electrically to a pixel electrode 167 of the organic EL. In addition, an insulating layer 168 is formed in a part in which a gate electrode wire 165 connected to the gate electrode 162 and a source electrode wire 155 connected to the source electrode 165 are crossed. Although not shown, the π electron conjugate system molecules as described in the Embodiment 1 are bonded chemically to the electrodes between the source electrode 165 and the semiconductor layer 164 and between the drain electrode 166 and the semiconductor layer 164.

Thus, a TFT with improved carrier mobility and driving voltage can be achieved stably by constructing an active matrix display using the TFT as described in the Embodiment 1. It enables a low cost display to be obtained as well. In addition, a sheet-like display having flexibility and impact resistance can be achieved by using an organic TFT. Still in addition, the improved carrier mobility enables to obtain an active matrix display with a fast display speed (a reaction rate).

Although a case in which a display screen uses an organic EL was described in this Embodiment, the present invention is not limited to this. The present invention is applicable to other active matrix displays provided with a circuit including a TFT, and the same effects can be obtained by them.

The configuration of the driving circuit that drives pixels is not limited to the configuration shown in this Embodiment. For example, in order to drive one pixel, the configuration in which a TFT for current driving is combined with a switching TFT for controlling the driving TFT may be employed. In addition, the configuration in which a plurality of TFTs is combined with each other may be employed. The TFTs are not limited to the ones shown in this Embodiment, and the same effects can be obtained by using the other TFTs of the present invention.

Next, a case in which the TFT of the present invention is applied to a wireless ID tag is described. A perspective view of an example of the wireless ID tag using the TFT of the present invention is schematically shown in FIG. 17.

Figure 17:
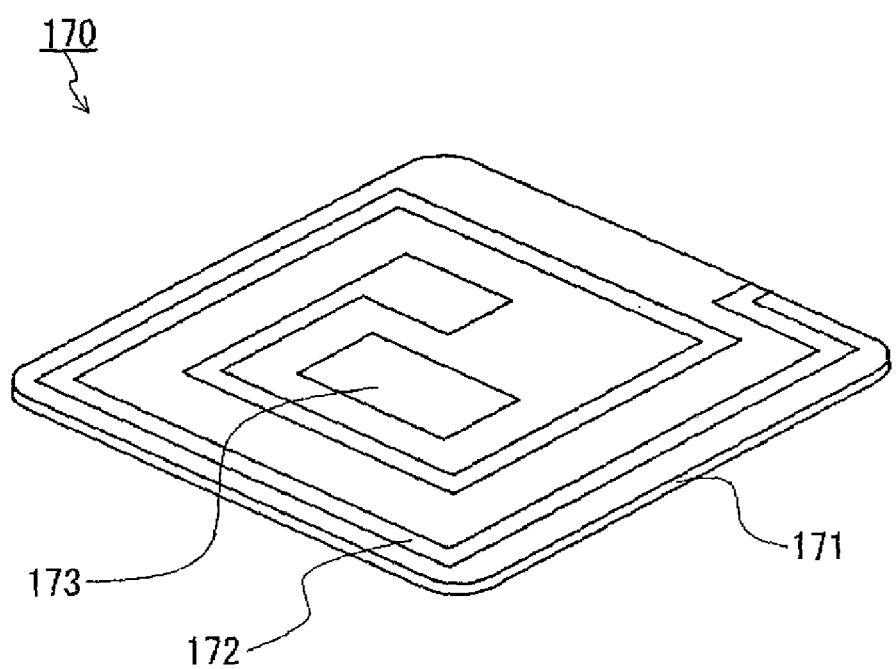
FIG. 17 is a perspective view that schematically shows a configuration of an example of the wireless ID tag.

As shown in FIG. 17, a wireless ID tag 170 employs a plastic substrate 171 in a form of film as its substrate. An antenna 172 and a memory IC 173 are provided on the substrate 171. Here, the memory IC 173 is constructed by using the TFT of the present invention as described in the Embodiment 1. The wireless ID tag 170 can be attached on a nonplanar object, such as a snack bag and a beverage can, by providing an adhesive property on the back face of the substrate. A protective film will be provided on the surface of the wireless ID tag 170 if required.

Thus, a wireless ID tag in various shapes that can be attached on objects of various materials can be obtained by using the TFT of the present invention. In addition, a wireless ID tag with a fast reaction rate (throughput speed) and a high communication frequency can be obtained by using the TFT of the present invention having excellent carrier mobility.

The wireless ID tag of the present invention is not limited to the wireless ID tag shown in FIG. 17. Thus, the layout and the configuration of the antenna and the memory IC are not limited. For example, a security circuit may be installed in the wireless ID tag.

Still in addition, although this Embodiment describes a case in which the antenna 172 and the memory IC 173 are formed on the plastic substrate 171, the present invention is not limited to this Embodiment. For example, the antenna 172 and the memory IC 173 may be formed directly on an intended object using a method such as an inkjet printing. In such a case as well, a wireless ID tag provided with a TFT improved carrier mobility and driving voltage can be manufactured at a reduced cost by forming the TFT of the present invention.

Then, a portable apparatus with an integrated circuit including the TFT of the present invention is described. Various elements using semiconductor characteristics, such as an arithmetic element, a storage element and a switching element, are employed for the integrated circuit of a portable apparatus. By using the TFT of the present invention for at least a part of these elements, a portable apparatus with the advantage of an organic material having excellent properties, such as mechanical flexibility, impact resistance, environmental resistance upon disposal, lightness, inexpensiveness, can be manufactured.

Figure 18:
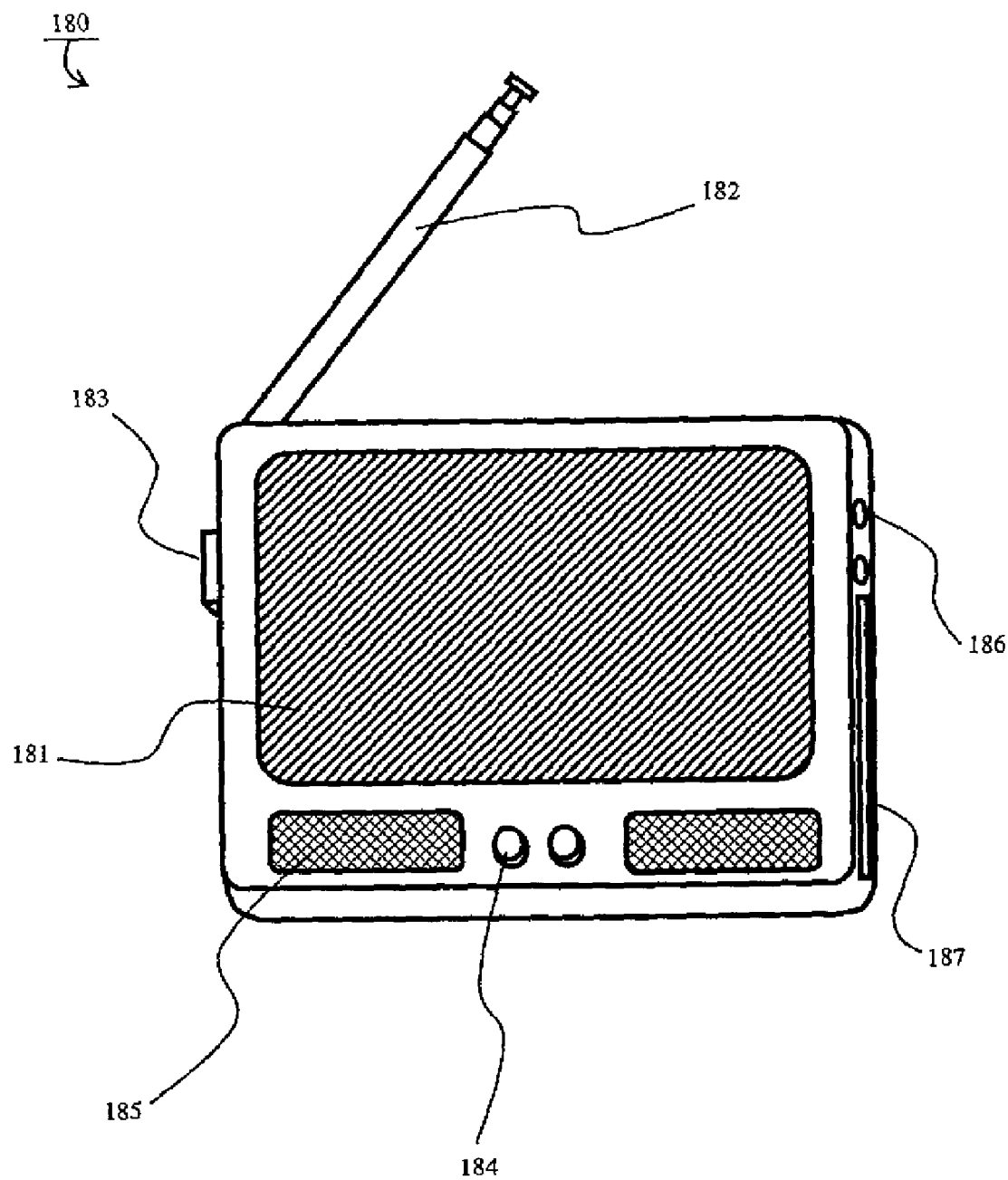
FIG. 18 is a perspective view that schematically shows a configuration of an example of the portable television.
Figure 19:
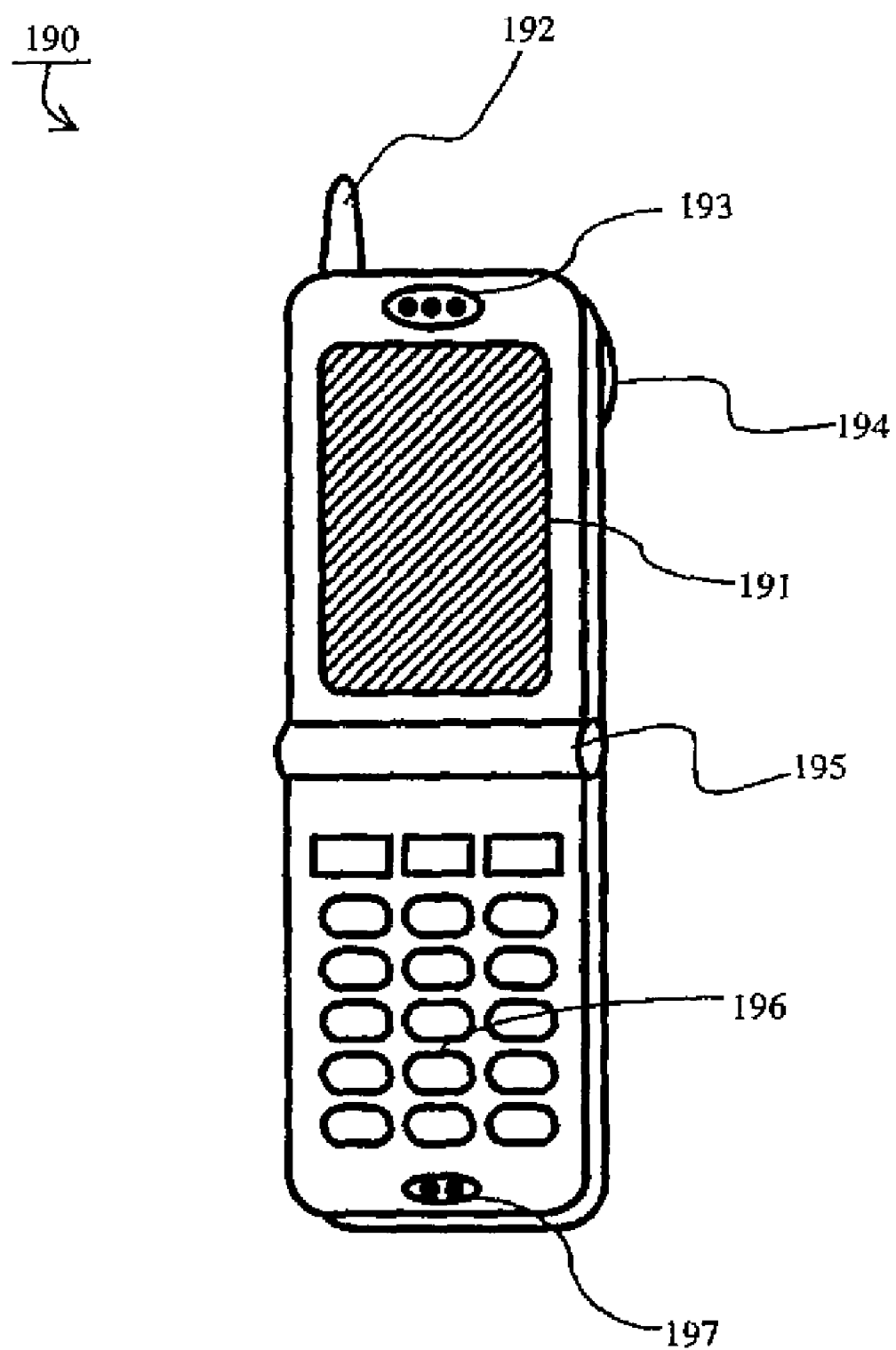
FIG. 19 is a perspective view that schematically shows a configuration of an example of the communication terminal.
Figure 20:
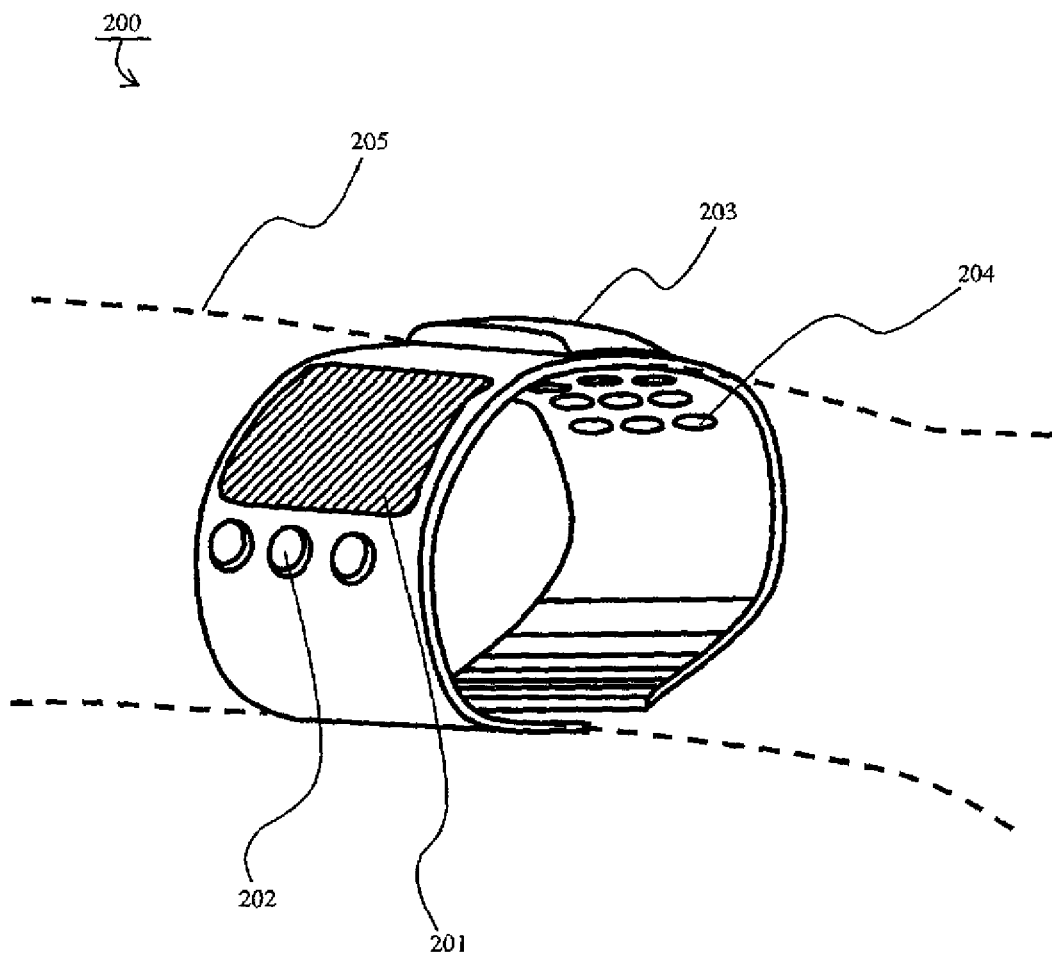
FIG. 20 is a perspective view that schematically shows a configuration of an example of the portable medical apparatus.

FIGS. 18 to 20 show three portable apparatuses as examples of the portable apparatus of the present invention.

A portable television 180 shown in FIG. 18 is provided with a display device 181, a receiving device 182, a side switch 183, front switches 184, sound output units 185, input/output devices 186 and a recording media insertion unit 187. An integrated circuit including the TFT of the present invention is used as a circuit including an element, such as an arithmetic element, a storage element and a switching element constructing the portable television 180.

A communication terminal 190 shown in FIG. 19 is provided with a display device 191, a transceiver 192, a voice output unit 193, a camera 194, a movable part for folding 195, operation switches 196 and a voice input unit 197. An integrated circuit including the TFT of the present invention is used as a circuit including an element, such as an arithmetic element, a storage element and a switching element constructing the communication terminal 190.

A portable medical apparatus 200 shown in FIG. 20 is provided with a display device 201, operation switches 202, a medical treatment unit 203 and a percutaneous contact unit 204. The portable medical apparatus 200 is carried by wrapping around an arm 205, for example. The medical treatment unit 203 is a part in which biological information obtained by the percutaneous contact unit 204 is processed and medical treatment, such as administration of medicine, is carried out through the percutaneous contact unit 204 according to the processed information. An integrated circuit including the TFT of the present invention is used as a circuit including an element, such as an arithmetic element, a storage element and a switching element constructing the portable medical apparatus 200.

Although the configuration of the portable apparatus to which the TFT of the present invention is applied is described with some examples, the present invention is not limited to these configurations. In addition, portable apparatuses to which the TFT of the present invention can be applied are not limited to the exemplified apparatuses. The TFT of the present invention can be applied favorably to an apparatus requiring properties, such as mechanical flexibility, impact resistance, environmental resistance upon disposal, lightness, inexpensiveness, which can be a PDA terminal, a wearable audio-visual system, a portable computer and a telecommunication apparatus in a form of wristwatch, for example.

Embodiment 3

The TFT of the present invention and the apparatus using the same were described in the Embodiments 1 and 2. Other electronic devices of the present invention are described in the Embodiment 3.

Figure 21:
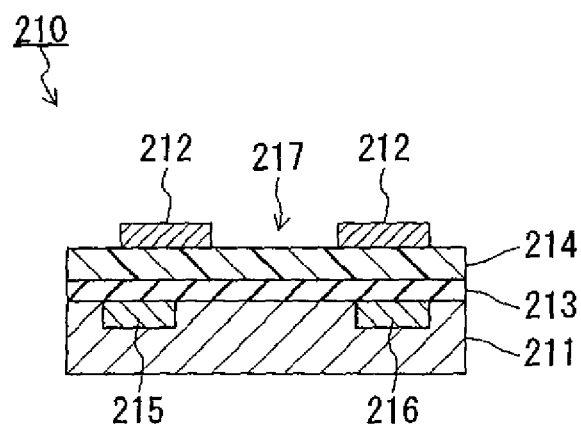
FIG. 21 is a cross-sectional view that schematically shows a configuration of an example of the sensor element.

As an example of the electronic device of the present invention, FIG. 21 schematically shows a cross-sectional view of a gas/ion sensor. In a sensor element 210 in FIG. 21, a variation of conductivity in an organic conductive layer is detected with high sensitivity as a variation of gate voltage by a Si—FET.

As shown in FIG. 21, a source electrode 215 and a drain electrode 216 are formed on a surface of a Si substrate 211, and an insulating layer 213 is formed to cover those. An organic conductive layer 214 is formed on the insulating layer 213, and gate electrodes 212 are formed on the organic conductive layer 214. Since the conductivity of the organic conductive layer 214 changes upon chemical absorption of gas or ions at a detection unit 217 and that results in a change of the gate voltage applied to the Si substrate 211 via the organic conductive layer 214 and the insulating layer 213, the amount of current flowing between the source electrode 215 and the drain electrode 216 is changed. Gas and ions can be detected by monitoring this variation in the amount of current.

The organic conductive layer 214 is formed by the first organic molecules described in the Embodiment 1, for example π electron conjugate system molecules, such as polythiophene. At the interface between the gate electrode 212 and the organic conductive layer 214, the second organic molecules described in the Embodiment 1 are chemically bonded with their π conjugate planes aligned to the gate electrodes 212 in order that the main π conjugate planes of them form a predetermined angle relative to the surfaces of the gate electrodes 212. Such a configuration enables an easy charge injection from the gate electrode 212. Thus, the driving voltage of the sensor can be lowered and the lifetime of the sensor can be extended. In addition, even when forming a plurality of sensors on the same plane such as an array sensor, an array sensor having smaller variations of elements can be achieved stably.

Although the gas/ion sensor was described as an example of the sensor element of the present invention, a sensor provided with an organic conductive layer includes other various sensors, such as humidity sensors, temperature sensors, optical sensors and pressure sensors. Any of such sensors uses changes in the physical property value of the organic conductive layer depending on the changes of the property of the sensing objectives, and thus sensing becomes possible by converting the change in the physical property value into an electrical value such as a current value. Accordingly, application of the present invention to these sensors enables an easy charge transfer between the electrodes and the organic conductive layer, and thus a sensor with excellent characteristics can be achieved stably.

Figure 22:
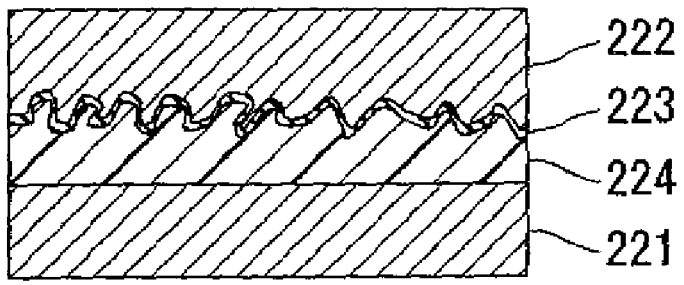
FIG. 22 is a cross-sectional view that schematically shows a configuration of an example of the capacitor.

As another example of the electronic device of the present invention, FIG. 22 schematically shows a cross-sectional view of an example of a capacitor. A capacitor 220 shown in FIG. 22 is an aluminum electrolytic capacitor employing $Al_2O_3$ as a dielectric. An anode 222 is Al, and a dielectric layer 223 made of $Al_2O_3$ is formed by electrochemically oxidizing a surface of the anode 222. In order to increase the capacity, a large number of pores are formed on the surface of the anode 222 by etching as shown in FIG. 22, and it is difficult to form a cathode 221 directly on a surface of the dielectric layer 223. For this reason, the cathode 221 is formed after an organic conductive layer 224 is formed as an intermediate layer.

Such capacitor elements have a problem that a frequency response of an impedance of the element is lowered when the resistance between the cathode 221 and the dielectric layer 223 is large. The present invention is applied in order to solve such a problem. Specifically, at the interface between the cathode 221 and the organic conductive layer 224, the second organic molecules described in the Embodiment 1 are chemically bonded with their π conjugate planes aligned to the cathode 221 in order that the main π conjugate planes of them form a predetermined angle relative to the surfaces of the cathode 221. In addition, the organic conductive layer 224 is formed by the first organic molecules described in the Embodiment 1, for example π electron conjugate system molecules such as polypyrrole. Since such a configuration enables an easy charge injection from the cathode 221, the resistance between the cathode 221 and the dielectric layer 223 can be reduced and thus a capacitor element with an excellent frequency response can be achieved easily.

Although the aluminum electrolytic capacitor is described as an example of a capacitor of the present invention, the present invention can be applied to secondary cells, other capacitors such as a tantalum electrolytic capacitor, or the like. Application of the present invention to these electronic devices enables an easy charge transfer between the electrodes and the organic conductive layer (intermediate electrode layer), and thus a capacitor, a secondary cell or the like with excellent characteristics can be achieved stably.

Figure 23:
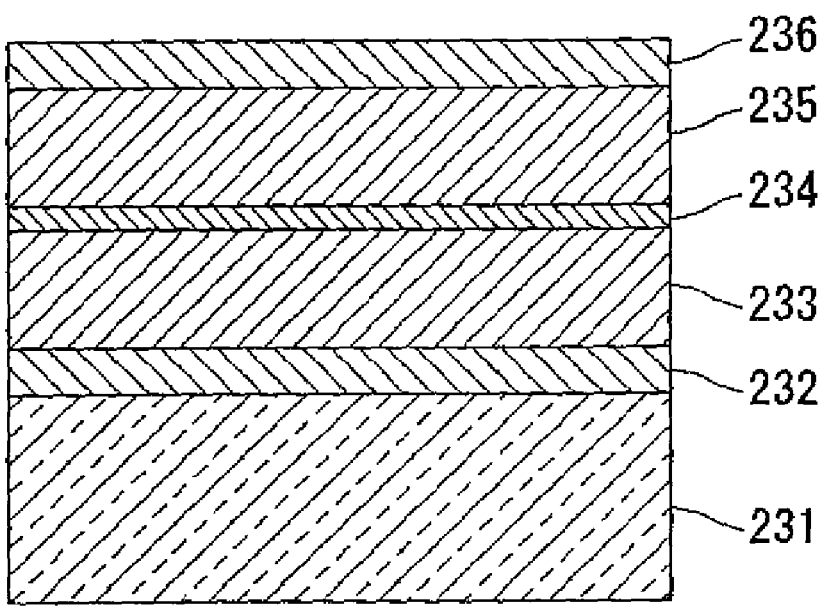
FIG. 23 is a cross-sectional view that schematically shows a configuration of an example of the laser.

FIG. 23 schematically shows a cross-sectional view of an example of an organic semiconductor laser as another example of the electronic device of the present invention. A semiconductor laser 230 in FIG. 23 is a laser known as thick film clad type and has basically the same structure as an organic LED. That is, a transparent electrode 232, a positive hole transport layer 233, a luminescent layer 234, an electron transport layer 235 and a metal electrode 236 are stacked successively on a glass substrate 231. In order to confine generated photons, the charge transport layers between which the luminescent layer 234 exists is employed as a clad layer. Thus, the charge transport layers are thicker than those in an organic LED.

Since the charge transport layers are thick, such laser elements have a problem of an increase of the driving voltage and an associated decrease of current density. The present invention is applied in order to solve such a problem. Specifically, at the interfaces between the transparent electrode 232 and the positive hole transport layer 232 and between the metal electrode 236 and the electron transport layer 235, the second organic molecules described in the Embodiment 1 are chemically bonded with their π conjugate planes aligned to the electrodes in order that the main π conjugate planes of them form a predetermined angle relative to the surfaces of the electrodes. In addition, the positive hole transport layer 233 and the electron transport layer 235 are formed by employing the first organic molecules described in the Embodiment 1, for example π electron conjugate system molecules such as a polythiophene derivative or a polyphenylene vinylene derivative. Since such a configuration enables an easy charge injection from each electrode, the driving voltage can be lowered and a laser element with excellent characteristics can be achieved easily.

Although the organic semiconductor laser of thick film clad type is described as an example of the laser element of the present invention, the present invention is not limited to this. In other organic semiconductor lasers as well, the ease of charge injection from an electrode to an organic semiconductor layer has a basic influence on its driving voltage. For this reason, an easier charge transfer between the electrode and the organic semiconductor layer by applying the present invention enables an organic semiconductor laser with excellent characteristics to be achieved stably.

The organic conductive layers, the electrodes and the electrode modifying layers of the electronic devices of the Embodiment 3 can be formed by the method described in the Embodiment 1.

Although the organic electronic devices of the present invention are described in the Embodiment 3 with specific examples as above, the present invention is not limited to them. The present invention can be applied to devices in which charge is transferred between an electrode and an organic molecule layer. An easy charge transfer is achieved by applying the present invention to such devices. In addition, application of the present invention enables a device with smaller variations in characteristics related to charge transfer to be manufactured.

[Method of Manufacturing the Second Organic Molecules]

An example of a method of manufacturing the compounds shown in FIGS. 5B, 5C, 7B, 12A and 14 is described below. The reactions mentioned in the following description (such as nitration reaction and sulfonation reaction) can be carried out under common conditions.

[Compound of FIG. 5B]

Figure 24:
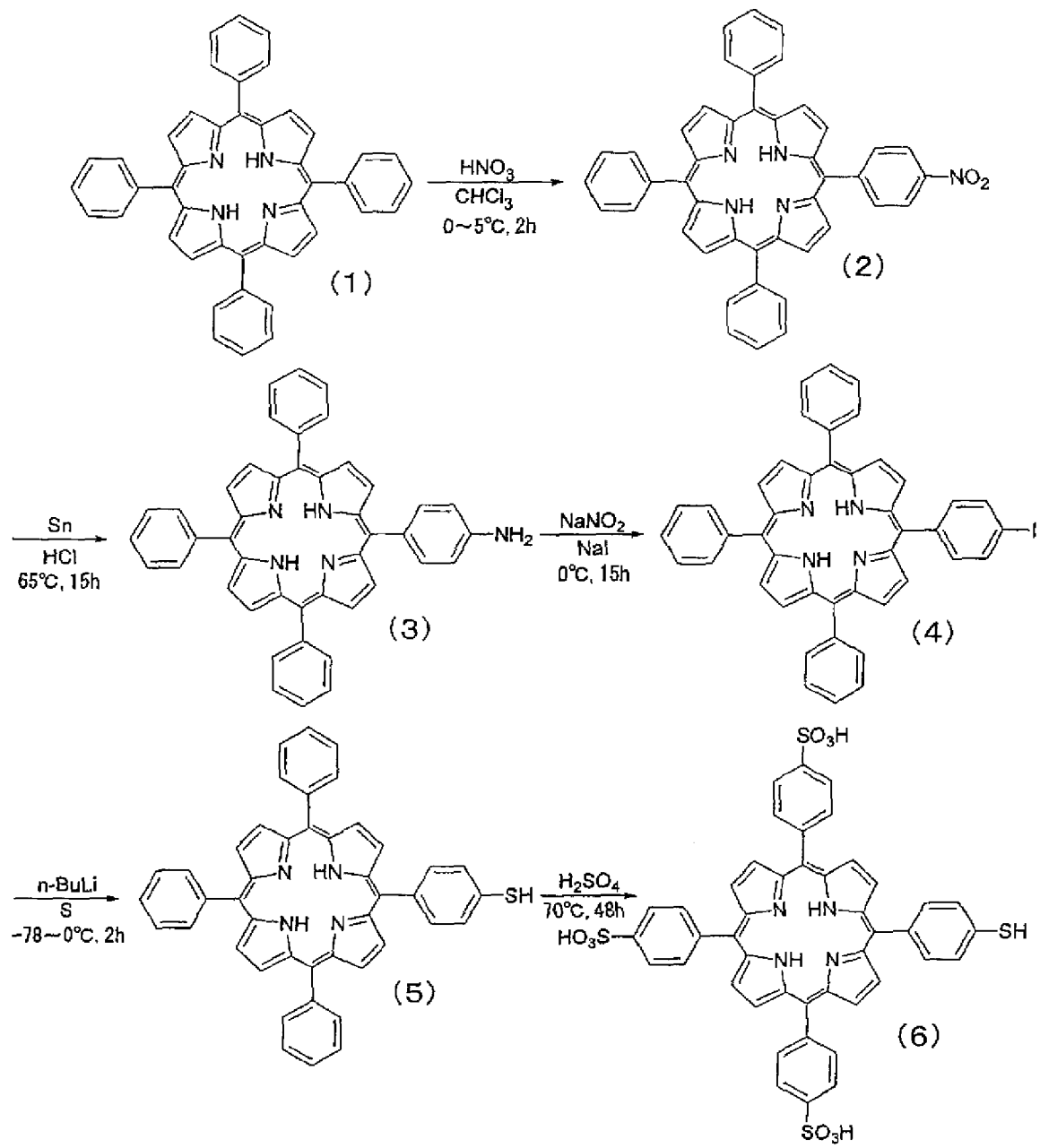
FIG. 24 is a drawing that shows an example of the synthesis method of the second organic molecule employed for the present invention.

A method of manufacturing the compound of FIG. 5B is shown in FIG. 24. First, a compound represented by the formula (2) is obtained by reaction of a compound represented by the formula (1) (tetraphenylporphyrin: Aldrich Corp.) and $HNO_3$. Next, a compound represented by the formula (3) is obtained by reaction of the compound represented by the formula (2) and HCl in the presence of Sn. Then, a compound represented by the formula (4) is obtained by reaction of the compound represented by the formula (3) and NaI in the presence of $NaNO_2$. Subsequently, a compound represented by the formula (5) is obtained by reaction of the compound represented by the formula (4) and sulfur in the presence of n-butyllithium. Subsequently, a compound represented by the formula (6) is obtained by reaction of the compound represented by the formula (5) and $H_2SO_4$. Finally, the compound of FIG. 5B can be obtained by turning the sulfonic acid group into sodium salt.

[Compound of FIG. 5C]

Figure 25:
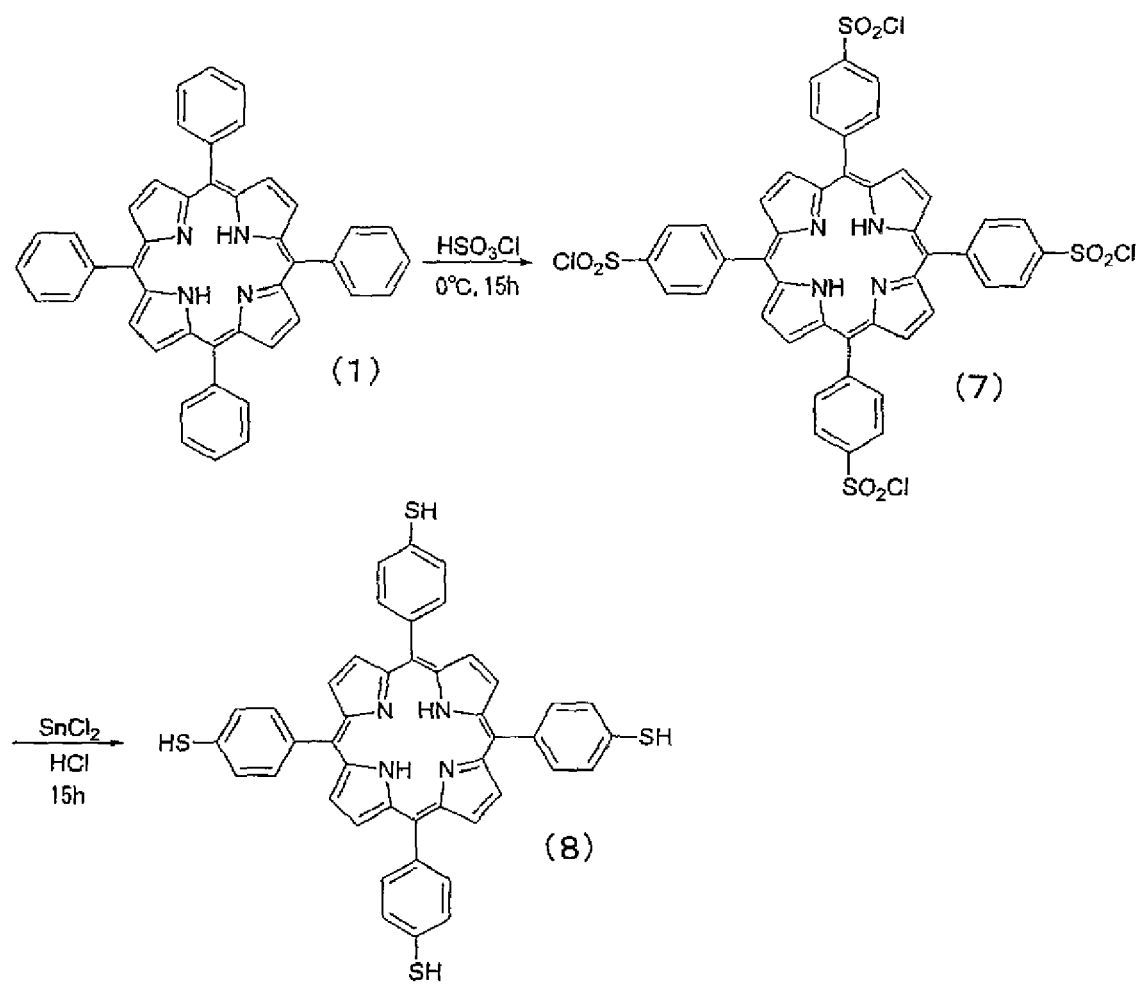
FIG. 25 is a drawing that shows another example of the synthesis method of the second organic molecule employed for the present invention.

A method of manufacturing the compound of FIG. 5C is shown in FIG. 25. First, a compound represented by the formula (7) is obtained by reaction of the compound represented by the formula (1) and $HSO_3Cl$. Next, the compound of FIG. 5C represented by the formula (8) is obtained by reaction of the compound represented by the formula (7) and HCl in the presence of $SnCl_2$.

[Compound of FIG. 7B]

Figure 26:
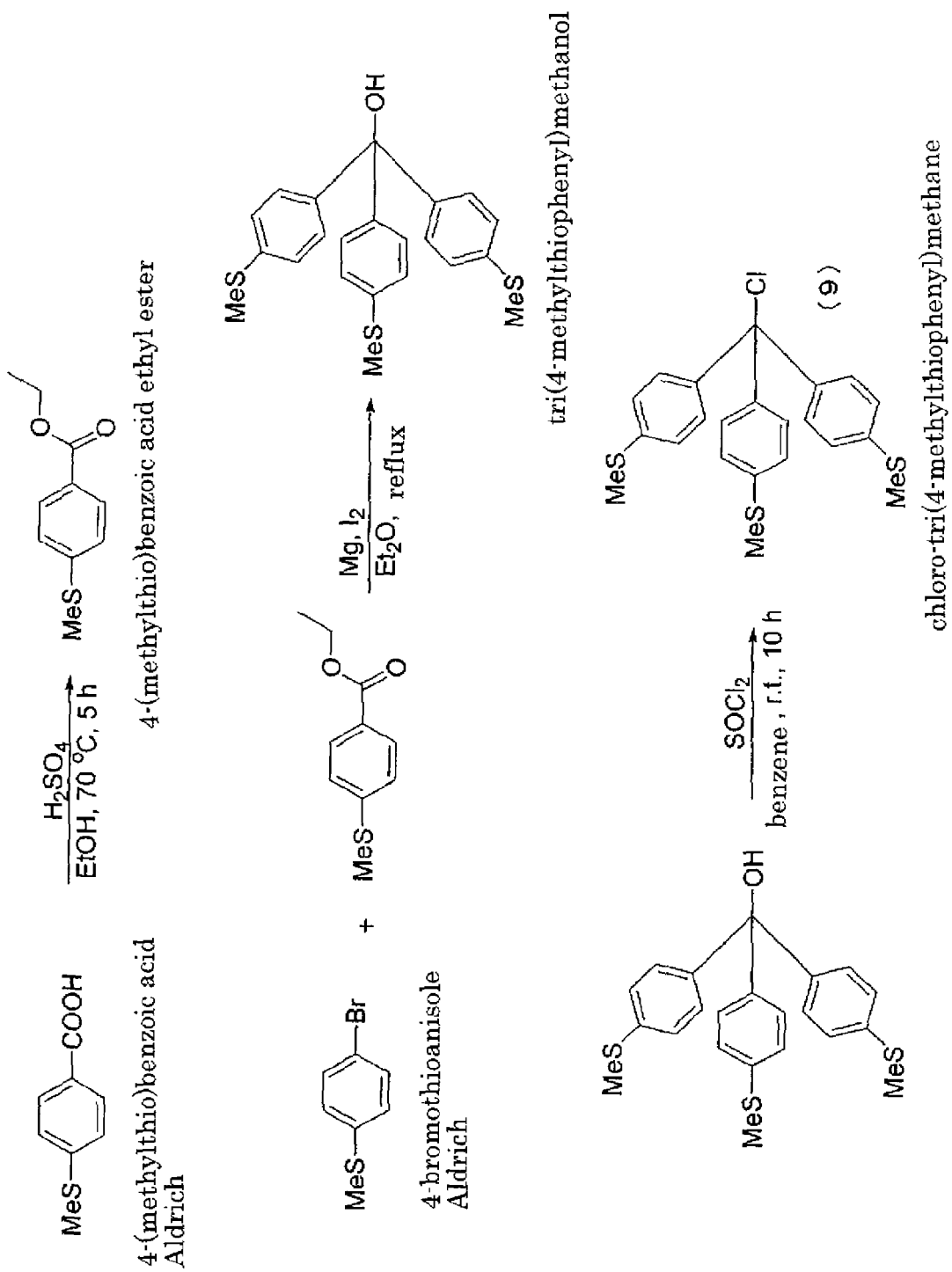
FIG. 26 is a drawing that shows another example of the synthesis method of the second organic molecule employed for the present invention.
Figure 27:
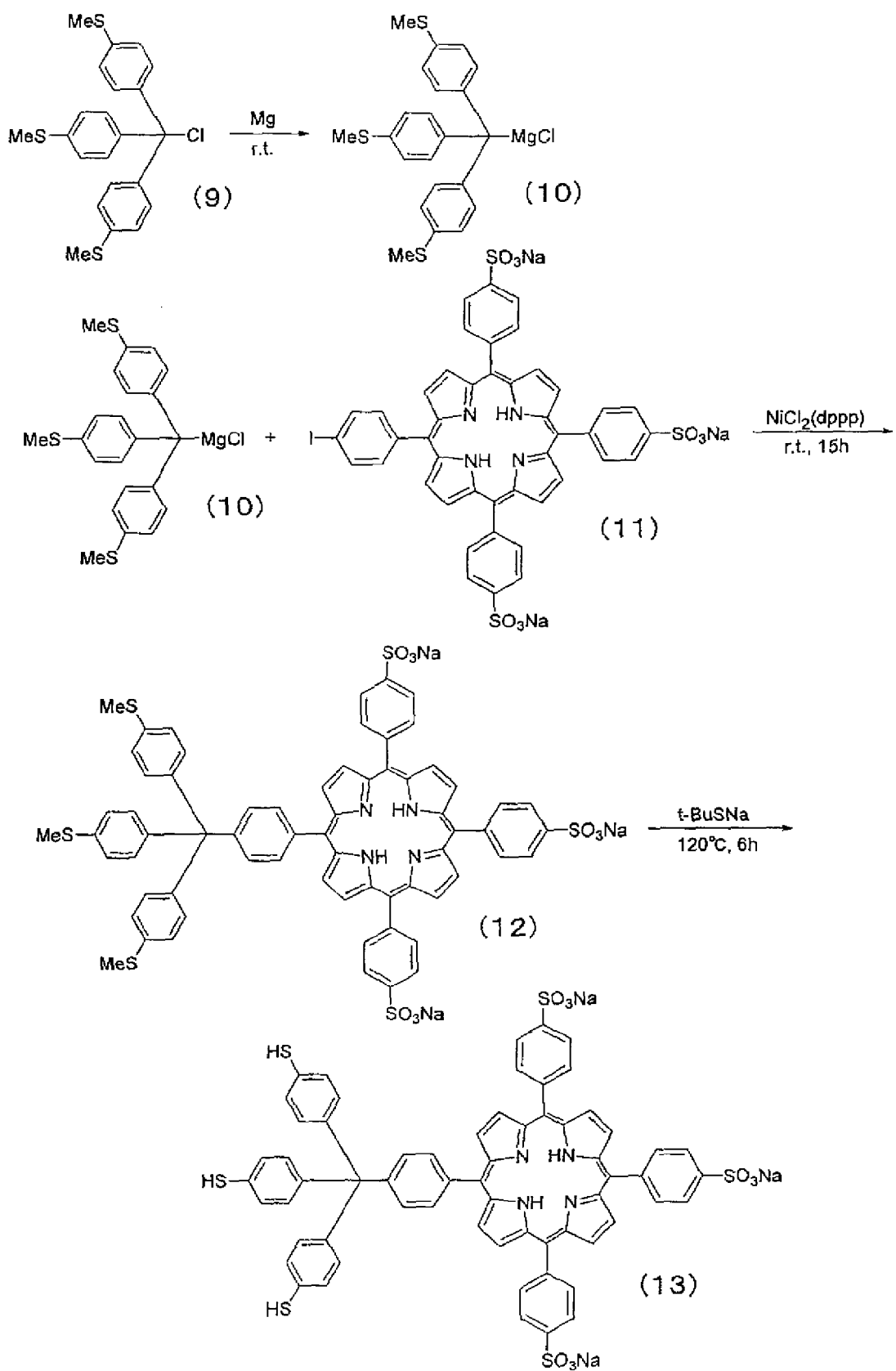
FIG. 27 is a drawing that shows the sequel to the synthesis method shown in FIG. 26.
Figure 28:
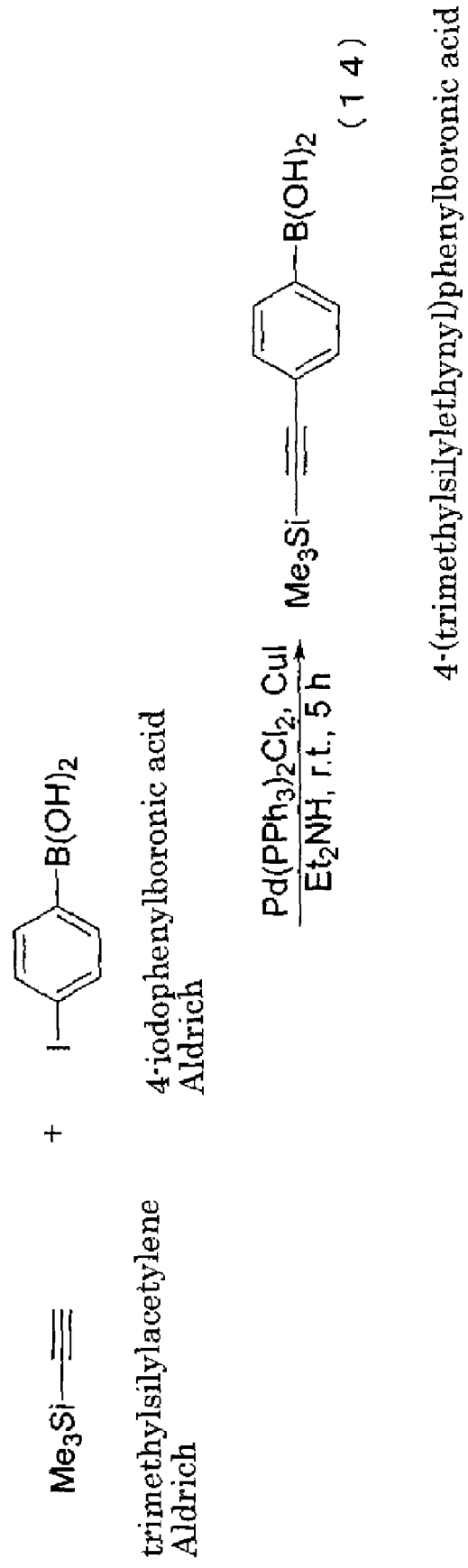
FIG. 28 is a drawing that shows another example of the synthesis method of the second organic molecule employed for the present invention.

A method of manufacturing the compound of FIG. 7B is shown in FIGS. 26 and 27. First, with 4-(methylthio)benzoic acid (Aldrich Corp.) as a starting material, a compound represented by the formula (9) is obtained by the reaction shown in FIG. 26.

Next, as shown in FIG. 27, a compound represented by the formula (10) is obtained by reaction of the compound represented by the formula (9) and magnesium at room temperature (r. t.). Then, a compound represented by the formula (12) is obtained by reaction of compounds represented by the formulas (10) and (11) in the presence of nickel. The compound represented by the formula (11) is obtained by sulfonating the compound represented by the formula (4) and then turning the sulfonic acid group into sodium salt. After that, the compound of FIG. 7B represented by the formula (13) is obtained by reaction of the compound represented by the formula (12) and $(CH_3)_3CSNa$.

[Compound of FIG. 12A]

A method of manufacturing the compound of FIG. 12A is shown in FIGS. 28 to 31. First, with trimethylsilylacetylene (Aldrich Corp.) and 4-iodophenylboronic acid (Aldrich Corp.) as starting materials, a compound represented by the formula (14) is obtained by a reaction shown in FIG. 28.

Figure 29:
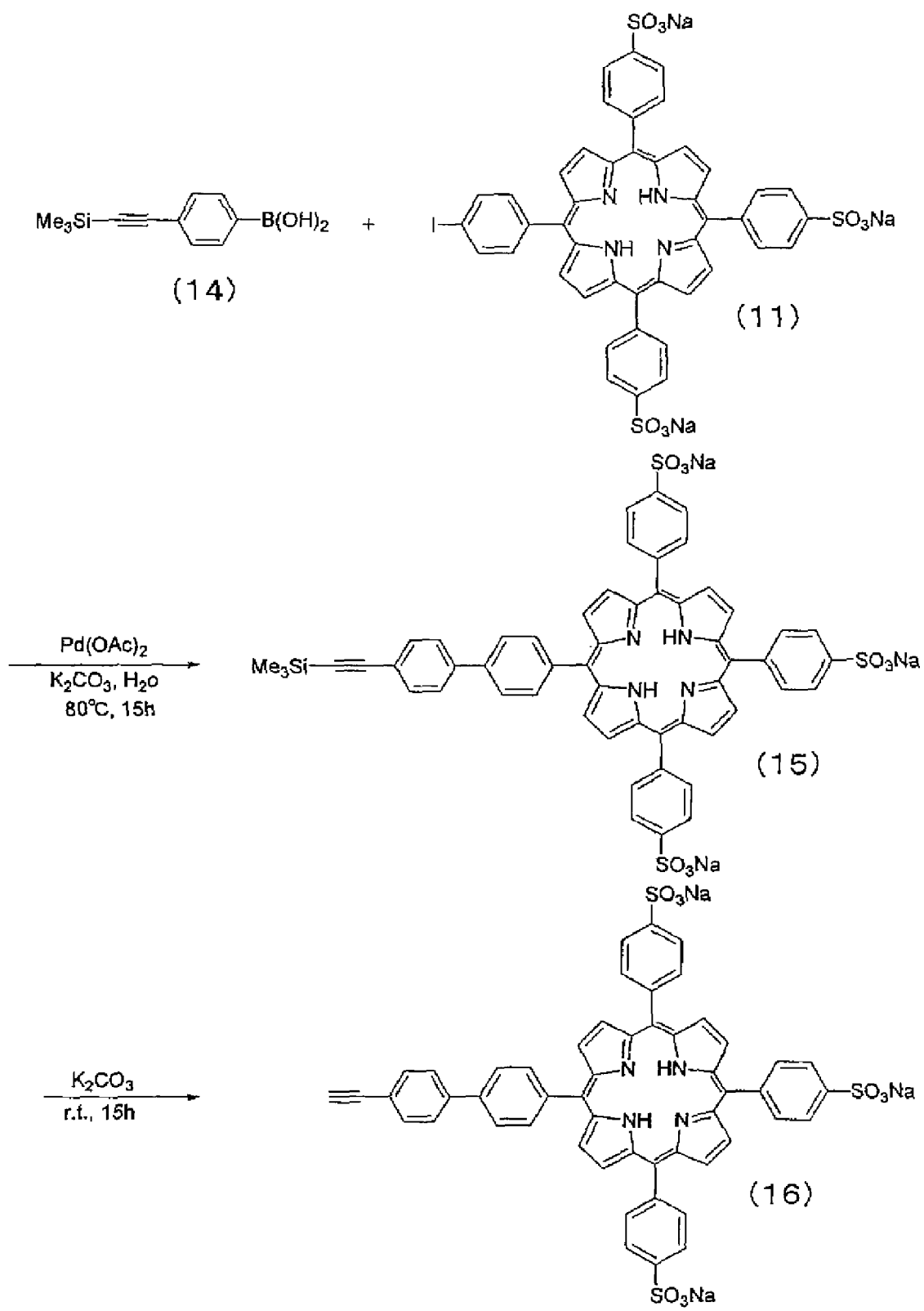
FIG. 29 is a drawing that shows the sequel to the synthesis method shown in FIG. 28.
Figure 30:
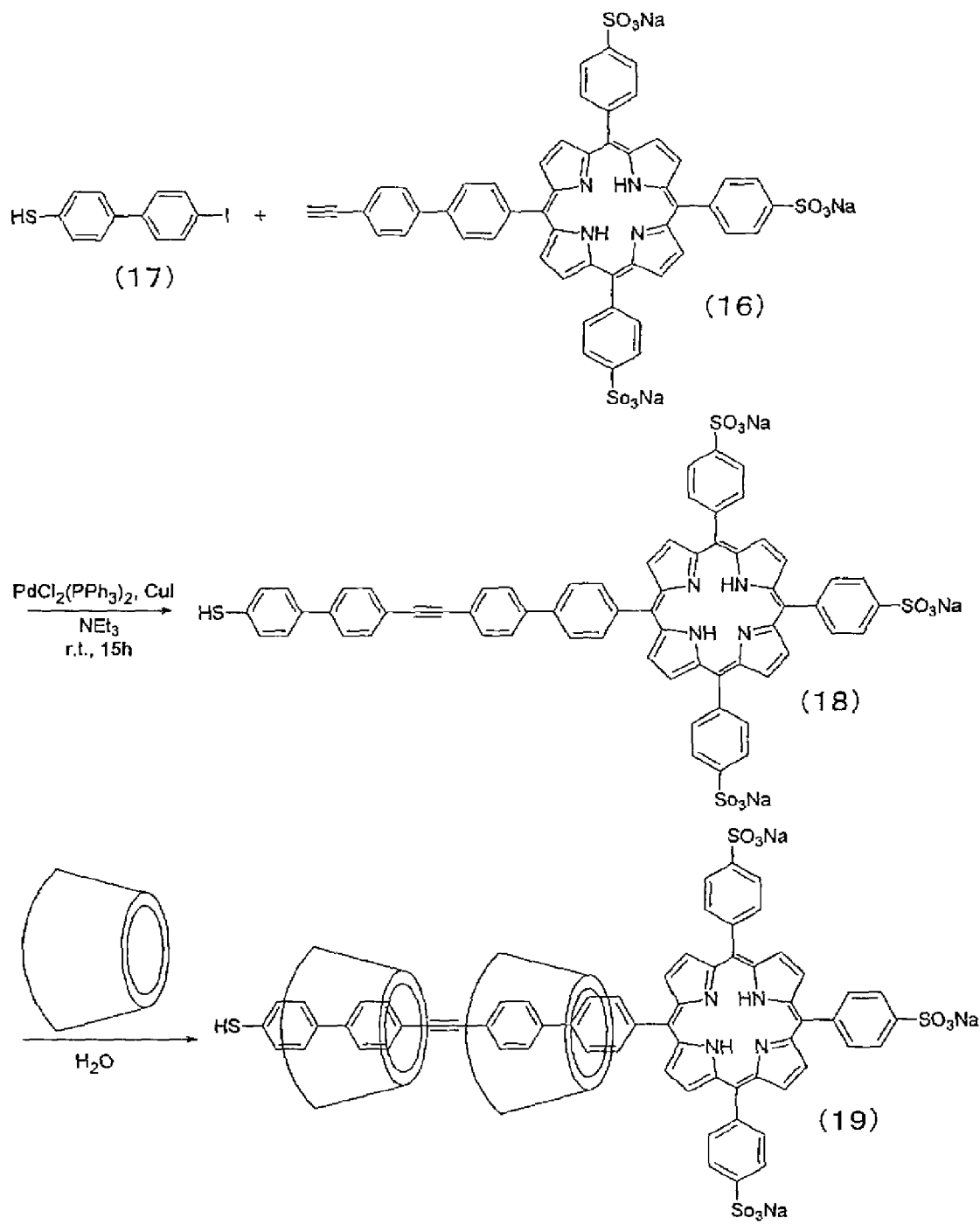
FIG. 30 is a drawing that shows the sequel to the synthesis method shown in FIG. 29.
Figure 31:
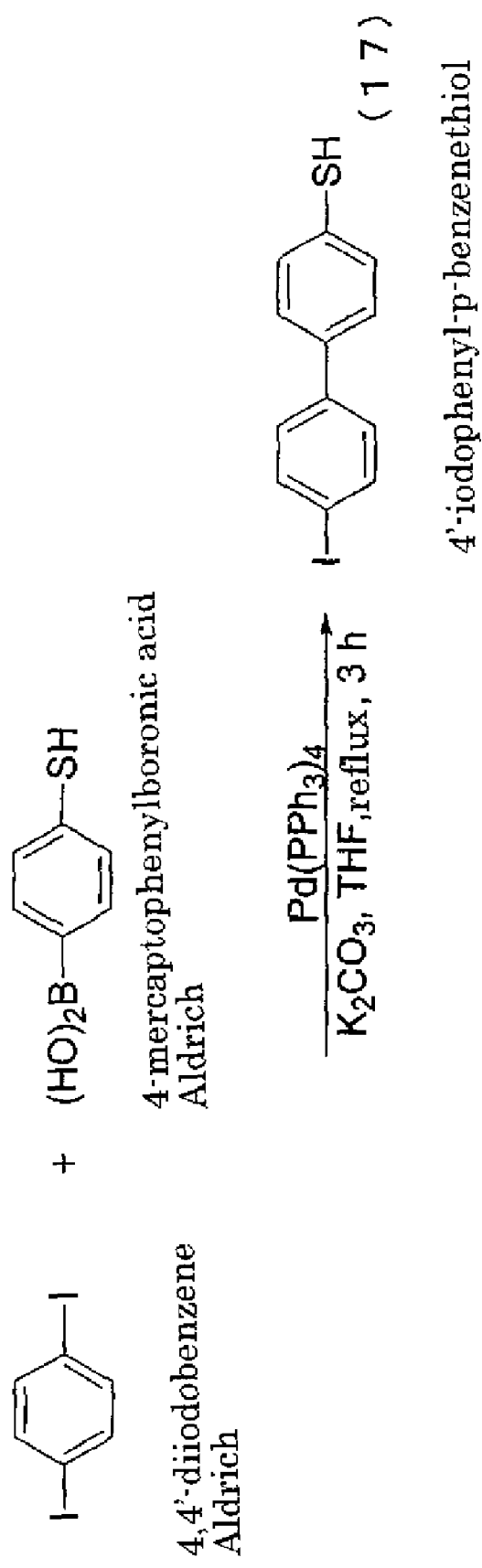
FIG. 31 is a drawing that shows the synthesis method of the compound employed for the synthesis method shown in FIG. 30.

Next, as shown in FIG. 29, a compound represented by the formula (15) is obtained by reaction of the compounds represented by the formulas (14) and (11) in the presence of diacetoxypalladium, $K_2CO_3$ and water. Then, a compound represented by the formula (16) is obtained by reaction of the compound represented by the formula (15) and $K_2CO_3$. Subsequently, as shown in FIG. 30, the compound of FIG. 12A represented by the formula (18) is obtained by reaction of the compounds represented by formulas (17) and (16) in the presence of Pd, cuprous iodide and triethylamine. The compound of the formula (17) is synthesized by a reaction of FIG. 31 with 4,4'-diiodobenzene (Aldrich Corp.) and 4-mercaptophenylboronic acid (Aldrich Corp.) as starting materials.

A clathrate compound shown by the formula (19) is obtained by mixing the compound of FIG. 12A and cyclodextrin in an aqueous solvent.

[Compound of FIG. 14]

Figure 32:
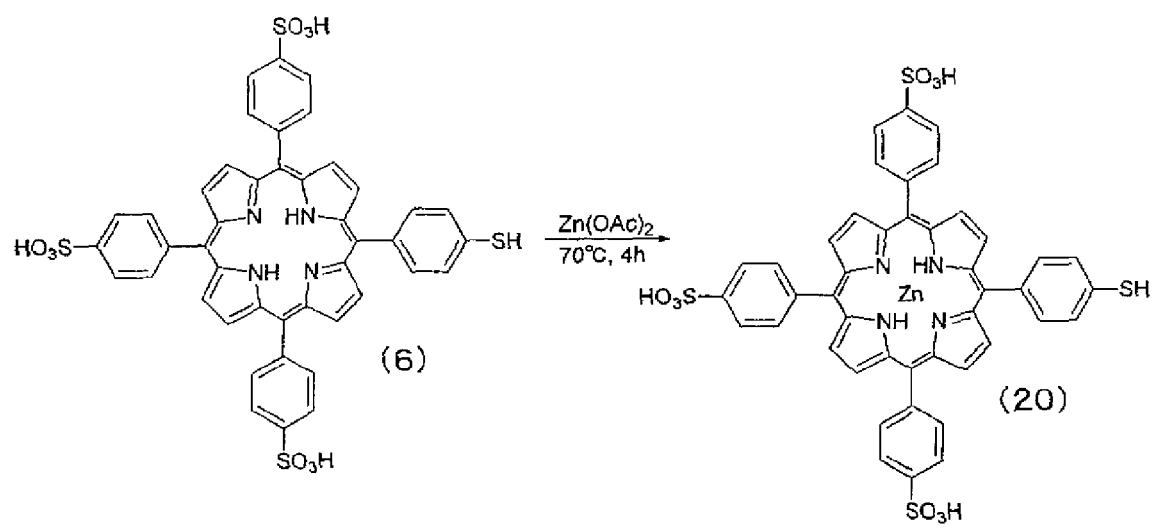
FIG. 32 is a drawing that shows another example of the synthesis method of the second organic molecule employed for the present invention.

A method of manufacturing the compound of FIG. 14 is shown in FIG. 32. The compound of FIG. 14 represented by the formula (20) is obtained by reaction of the compound represented by the formula (6) and diacetoxyzinc.

The invention may be embodied in other forms without departing from the spirit or essential characteristics thereof. The embodiments disclosed in this specification are to be considered in all respects as illustrative and not limiting. The scope of the invention is indicated by the appended claims rather than by the foregoing description, and all changes that come with the meaning and range of equivalency of the claims are intended to be embraced therein.

INDUSTRIAL APPLICABILITY

The present invention is applicable to an organic electric device in which charge is transferred between an electrode and an organic molecule layer and to a method of manufacturing the same. In addition, the present invention is applicable to various types of apparatuses provided with such an organic electronic device.

The invention claimed is:

1. An electronic device, comprising:
at least one electrode; and
an organic molecule layer formed adjacent to the electrode in which charge transfers between the layer and the electrode,
wherein the organic molecule layer includes a plurality of first organic molecules containing a conjugated π electron that composes a π conjugate plane (A),
a plurality of second organic molecules is bonded chemically to a surface of the electrode at an interface between the electrode and the organic molecule layer,
the second organic molecule contains a conjugated π electron that composes a π conjugate plane (B),
the second organic molecule is a molecule having a structure in which the π conjugate plane (B) and the surface of the electrode form an angle within a predetermined range when the second organic molecule is bonded chemically to the surface of the electrode, and
an angle formed by the π conjugate planes (A) and (B) is within a range from 0° to 30°.

2. The electronic device according to claim 1, wherein the angle formed by the π conjugate plane (B) and the surface of the electrode is within a range from 0° to 15° or a range from 75° to 90°.

3. The electronic device according to claim 1, wherein the conjugated π electron composing the π conjugate plane (B) exists in a condensed ring structure or a macrocyclic structure.

4. The electronic device according to claim 1, wherein the second organic molecule forms a monomolecular layer.

5. The electronic device according to claim 1, wherein the second organic molecule is bonded to a plurality of atoms of the surface of the electrode.

6. The electronic device according to claim 1, wherein the second organic molecule is insulated by a cyclic molecule.

7. The electronic device according to claim 1, wherein the second organic molecule is bonded to the atom of the surface of the electrode via a sulfur atom.

8. The electronic device according to claim 1, wherein the second organic molecule is porphyrin.

9. The electronic device according to claim 1, wherein the organic molecule layer is an organic semiconductor layer.

10. The electronic device according to claim 1, further comprising a gate electrode that applies an electric field to the organic molecule layer,
 the electrode is at least one electrode selected from a source electrode and a drain electrode,
 the organic molecule layer forms a channel region, and
 the electronic device functioning as a field-effect transistor.

11. The electronic device according to claim 7, wherein the sulfur atom is derived from a mercapto group bonded to the $\pi$ conjugate plane (B).

12. The electronic device according to claim 1, wherein the first organic molecules are not bonded to the surface of the electrode, and
 the second organic molecules are not included in the organic molecule layer.

13. The electronic device according to claim 1, wherein the second organic molecules are in contact with the organic molecule layer.

14. An electronic device, comprising:
 at least one electrode; and
 an organic molecule layer formed adjacent to the electrode in which charge transfers between the layer and the electrode,
 wherein the organic molecule layer includes a plurality of first organic molecules containing a conjugated $\pi$ electron that composes a $\pi$ conjugate plane (A),
 a plurality of second organic molecules is bonded chemically to a surface of the electrode at an interface between the electrode and the organic molecule layer,
 the second organic molecule contains a conjugated $\pi$ electron that composes a $\pi$ conjugate plane (B),
 the second organic molecule is a molecule having a structure in which the $\pi$ conjugate plane (B) and the surface of the electrode form an angle within a predetermined range when the second organic molecule is bonded chemically to the surface of the electrode, and
 the $\pi$ conjugate plane (A) is adjacent to the $\pi$ conjugate plane (B) so that the $\pi$ conjugate plane (A) and the $\pi$ conjugate plane (B) form an angle within a predetermined range.

15. The electronic device according to claim 14, wherein the angle formed by the $\pi$ conjugate plane (B) and the surface of the electrode is within a range from 0° to 15° or a range from 75° to 90°.

16. The electronic device according to claim 14, wherein the conjugated $\pi$ electron composing the $\pi$ conjugate plane (B) exists in a condensed ring structure or a macrocyclic structure.

17. The electronic device according to claim 14, wherein the second organic molecule forms a monomolecular layer.

18. The electronic device according to claim 14, wherein the second organic molecule is bonded to a plurality of atoms of the surface of the electrode.

19. The electronic device according to claim 14, wherein the second organic molecule is insulated by a cyclic molecule.

20. The electronic device according to claim 14, wherein the second organic molecule is bonded to the atom of the surface of the electrode via a sulfur atom.

21. The electronic device according to claim 14, wherein the second organic molecule is porphyrin.

22. The electronic device according to claim 14, wherein the organic molecule layer is an organic semiconductor layer.

23. The electronic device according to claim 14, further comprising a gate electrode that applies an electric field to the organic molecule layer,
 the electrode is at least one electrode selected from a source electrode and a drain electrode,
 the organic molecule layer forms a channel region, and
 the electronic device functioning as a field-effect transistor.

24. The electronic device according to claim 20, wherein the sulfur atom is derived from a mercapto group bonded to the $\pi$ conjugate plane (B).

25. The electronic device according to claim 14, wherein the first organic molecules are not bonded to the surface of the electrode, and
 the second organic molecules are not included in the organic molecule layer.

26. The electronic device according to claim 14, wherein the second organic molecules are in contact with the organic molecule layer.

27. An electronic device, comprising:
 at least one electrode; and
 an organic molecule layer formed adjacent to the electrode in which charge transfers between the layer and the electrode,
 wherein the organic molecule layer includes a plurality of first organic molecules containing a conjugated $\pi$ electron that composes a $\pi$ conjugate plane (A),
 a plurality of second organic molecules is bonded chemically to a surface of the electrode at an interface between the electrode and the organic molecule layer,
 the second organic molecule contains a conjugated $\pi$ electron that composes a $\pi$ conjugate plane (B),
 the second organic molecule is a molecule having a structure in which the $\pi$ conjugate plane (B) and the surface of the electrode form an angle within a predetermined range when the second organic molecule is bonded chemically to the surface of the electrode, and
 the angle formed by the $\pi$ conjugate plane (B) and the surface of the electrode is within a range from 0° to 15° or a range from 75° to 90°.

28. The electronic device according to claim 27, wherein the conjugated $\pi$ electron composing the $\pi$ conjugate plane (B) exists in a condensed ring structure or a macrocyclic structure.

29. The electronic device according to claim 27, wherein the second organic molecule forms a monomolecular layer.

30. The electronic device according to claim 27, wherein the second organic molecule is bonded to a plurality of atoms of the surface of the electrode.

31. The electronic device according to claim 27, wherein the second organic molecule is insulated by a cyclic molecule.

32. The electronic device according to claim 27, wherein the second organic molecule is bonded to the atom of the surface of the electrode via a sulfur atom.

33. The electronic device according to claim 27, wherein the second organic molecule is porphyrin.

34. The electronic device according to claim 27, wherein the organic molecule layer is an organic semiconductor layer.

35. The electronic device according to claim 27, further comprising a gate electrode that applies an electric field to the organic molecule layer,
    the electrode is at least one electrode selected from a source electrode and a drain electrode,
    the organic molecule layer forms a channel region, and
    the electronic device functioning as a field-effect transistor.

36. The electronic device according to claim 32, wherein the sulfur atom is derived from a mercapto group bonded to the π conjugate plane (B).

37. The electronic device according to claim 27, wherein the first organic molecules are not bonded to the surface of the electrode, and
    the second organic molecules are not included in the organic molecule layer.

38. The electronic device according to claim 27, wherein the second organic molecules are in contact with the organic molecule layer.

* * * * *